US012649826B2

(12) United States Patent
Moon et al.

(10) Patent No.: US 12,649,826 B2
(45) Date of Patent: Jun. 9, 2026

(54) POLYETHYLENE GLYCOL DERIVATIVE, COMPOSITION COMPRISING SAME, AND METHOD FOR PREPARING BIOACTIVE POLYPEPTIDE CONJUGATE BY USING SAME

(71) Applicants: HANMI FINE CHEMICAL CO., LTD., Siheung-si (KR); HANMI PHARM. CO., LTD., Hwaseong-si (KR)

(72) Inventors: Ji Hye Moon, Hwaseong-si (KR); Yeon Jeong Jang, Hwaseong-si (KR); Hyun Jung Shim, Hwaseong-si (KR); Eun Hye Kim, Hwaseong-si (KR); Tae In Eom, Hwaseong-si (KR); Su Mi Lee, Hwaseong-si (KR); Yu Rim Kim, Siheung-si (KR); Yong Gyu Jung, Siheung-si (KR); Ji Hye Kim, Siheung-si (KR); Soon Ah Ahn, Siheung-si (KR); Wok Chul Yoo, Siheung-si (KR); Young Bum Cho, Siheung-si (KR); Kyoung Min Lee, Siheung-si (KR); Jae Heon Lee, Siheung-si (KR)

(73) Assignees: HANMI FINE CHEMICAL CO., LTD., Siheung-si (KR); HANMI PHARM. CO., LTD., Hwaseong-si (KR)

( * ) Notice: Subject to any disclaimer, the term of this patent is extended or adjusted under 35 U.S.C. 154(b) by 707 days.

(21) Appl. No.: 18/026,481

(22) PCT Filed: Sep. 16, 2021

(86) PCT No.: PCT/KR2021/012717
§ 371 (c)(1),
(2) Date: Mar. 15, 2023

(87) PCT Pub. No.: WO2022/060131
PCT Pub. Date: Mar. 24, 2022

(65) Prior Publication Data

US 2023/0357501 A1 Nov. 9, 2023

(30) Foreign Application Priority Data

Sep. 16, 2020 (KR) ........................ 10-2020-0119259

(51) Int. Cl.

| | |
|---|---|
| ***A61K 47/60*** | (2017.01) |
| ***A61K 38/16*** | (2006.01) |
| ***C08G 65/331*** | (2006.01) |

(52) U.S. Cl.
CPC .......... *C08G 65/3312* (2013.01); *A61K 38/16* (2013.01); *A61K 47/60* (2017.08)

(58) Field of Classification Search
CPC .. C08G 65/3312; C08G 65/331; A61K 38/16; A61K 47/60; A61K 38/193; A61K 38/26; A61K 47/68; A61K 47/6811; A61K 47/6889
See application file for complete search history.

(56) References Cited

U.S. PATENT DOCUMENTS

| | | | | |
|---|---|---|---|---|
| 6,465,694 | B1 * | 10/2002 | Baudys | C07C 227/18 568/494 |
| 6,924,264 | B1 | 8/2005 | Prickett et al. | |
| 9,981,017 | B2 | 5/2018 | Song et al. | |
| 10,660,940 | B2 | 5/2020 | Jang et al. | |
| 2004/0062746 | A1 | 4/2004 | Martinez et al. | |
| 2005/0191301 | A1 | 9/2005 | Heavner et al. | |
| 2019/0040196 | A1 * | 2/2019 | Kim | C08G 65/331 |
| 2020/0283492 | A1 | 9/2020 | Lee et al. | |

FOREIGN PATENT DOCUMENTS

| | | | |
|---|---|---|---|
| CN | 111406073 | A | 7/2020 |
| JP | 7-316285 | A | 12/1995 |
| JP | 2003-268099 | A | 9/2003 |
| KR | 10-2009-0118626 | A | 11/2009 |
| KR | 10-2017-0100842 | A | 9/2017 |
| KR | 10-2019-0038456 | A | 4/2019 |
| RU | 2519073 | C1 | 6/2014 |
| RU | 2 677 796 | C9 | 1/2019 |
| WO | 2006/076471 | A2 | 7/2006 |
| WO | 2017/131496 | A1 | 8/2017 |

OTHER PUBLICATIONS

Chinese Office Action dated Jul. 7, 2025, issued in Chinese application No. 202180063303.6.
Communication with Search Report issued Sep. 11, 2024 in Russian Patent Application No. 2023105036.
International Search Report for PCT/KR2021/012717 dated Dec. 24, 2021.
Communication dated Nov. 25, 2025 issued by the Patent Office of the Russian Federation: Federal Institute of Industrial Property in application No. 2025107086/10.

* cited by examiner

*Primary Examiner* — Kumar R Bhushan
(74) *Attorney, Agent, or Firm* — Sughrue Mion, PLLC

(57) ABSTRACT

A polyethylene glycol derivative compound is represented by Formula 1 described in the detailed description. In Formula 1, n is a natural number of 30 to 115, and $R^1$ and $R^2$ are $C_1$ to $C_5$ alkyl that are identical to or different from each other.

20 Claims, 10 Drawing Sheets

Specification includes a Sequence Listing.

POLYETHYLENE GLYCOL DERIVATIVE, COMPOSITION COMPRISING SAME, AND METHOD FOR PREPARING BIOACTIVE POLYPEPTIDE CONJUGATE BY USING SAME

CROSS REFERENCE TO RELATED APPLICATIONS

This application is a National Stage of International Application No. PCT/KR2021/012717 filed Sep. 16, 2021, claiming priority based on Korean Patent Application No. 10-2020-0119259 filed Sep. 16, 2020.

INCORPORATION BY REFERENCE OF SEQUENCE LISTING

The content of the electronically submitted sequence listing, file name: Q285409_SEQ_LIST_AS_FILED.txt; size: 5,003 bytes; and date of creation: May 15, 2023, filed herewith, is incorporated herein by reference in its entirety.

TECHNICAL FIELD

The present disclosure relates to a polyethylene glycol derivative, a composition including the same, and a method of preparing a physiologically active polypeptide conjugate using the polyethylene glycol derivative.

BACKGROUND ART

Peptide drugs are substances in which two or more amino acids are linked via a certain chemical bond, and are mainly produced through chemical synthesis. It is known that peptide drugs have the characteristics of 'biocompatibility' and 'in vivo specificity' so that they can exhibit strong pharmacological action and activity even in small amounts while having small side effects. Therefore, peptide drugs are expected to compensate for the shortcomings of synthetic drugs and protein drugs.

However, peptide drugs are easily decomposed into amino acids by protein enzymes in the digestive tract, making them unsuitable for oral administration, and thus should be delivered through injection. Also, due to their short half-life in blood, peptide drugs have low bioavailability and need to be repeatedly administered. In addition, since they have a smaller size than protein drugs, the peptide drugs do not reach the target when administered, and are rapidly eliminated from the body through the kidneys.

In order to solve this problem, various methods have been studied including: a method in which the bio-membrane permeability of a peptide drug is increased to deliver the same into the body by inhalation through the oral or nasal cavity; a method in which a specific amino acid sequence, sensitive to a proteolytic enzyme, is changed to inhibit the degradation of peptides by proteolytic enzymes; and a method of preparing a fusion protein of a physiologically active polypeptide and human serum albumin or an immunoglobulin fragment (Fc) by using recombinant fusion technology; and a method of chemically adding a highly soluble non-peptide polymer onto the peptide surface, etc.

Polyethylene glycol (PEG), which is a non-peptidyl polymer, is a nonionic, nontoxic, biocompatible and highly hydrophilic polymer. Since PEG can be easily modified chemically, it is possible to inhibit loss by the kidneys and protect the drug from proteolytic enzymes by increasing the molecular weight of the drug by covalently attaching the same onto a peptide or a protein drug. Since PEG does not cause any particular side effects, it is being actively studied as a method for extending the half-life of peptide drugs in blood.

PEG has been approved by the U.S. Food and Drug Administration as 'Generally Recognized as Safe (GRAS)'. WO 06/076471 describes the continuation of physiological activity by binding PEG to a B-type natriuretic peptide (BNP) used as a treatment for congestive heart failure. U.S. Pat. No. 6,924,264 describes a method of increasing the duration in vivo by binding PEG to a lysine residue of exendin-4.

Homopolymers of ethylene glycol, which is a PEG that is not modified or deformed, have hydroxyl groups at either or both ends. A PEG derivative may be used for binding to a drug. For example, a PEG derivative in which hydroxyl groups at one or both ends of the PEG chain are converted into highly reactive functional groups, may be used. For example, as the PEG derivative, PEG-aldehyde, PEG-acetaldehyde, PEG-propionaldehyde, and the like may be used. These aldehyde PEG derivatives may be conjugated with a peptide drug by selective reaction of an aldehyde group at an end thereof with an end of an amino acid of a protein to form a chemical bond with the peptide drug.

However, in case using PEG derivatives having both ends being aldehyde groups, both aldehyde groups may participate in the reaction, resulting in the generation of unwanted adducts or excessive use of PEG, which in turn adversely affects the yield and purity.

DESCRIPTION OF EMBODIMENTS

Technical Problem

The present disclosure is to provide a polyethylene glycol derivative that can be used in the preparation of peptide drugs and a composition including the same.

The present disclosure is also to provide a method for preparing a physiologically active polypeptide conjugate by using the polyethylene glycol derivative.

Solution to Problem

A polyethylene glycol derivative compound according to an embodiment is represented by Formula 1:

Formula 1

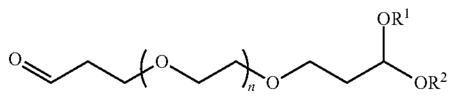

wherein, in Formula 1, n is a natural number of 30 to 115, and $R^1$ and $R^2$ may be $C_1$ to $C_5$ alkyl that are identical to or different from each other.

The $C_1$ to $C_5$ alkyl may be methyl, ethyl, propyl, or butyl.

$R^1$ and $R^2$ may be ethyl.

n may be a natural number from 50 to 100.

n may be a natural number from 67 to 83.

A polyethylene glycol derivative composition according to an aspect may include:

a polyethylene glycol derivative represented by Formula 1A;

a polyethylene glycol derivative represented by Formula 2; and a polyethylene glycol derivative represented by Formula 3:

Formula 1A

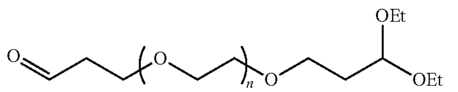

Formula 2

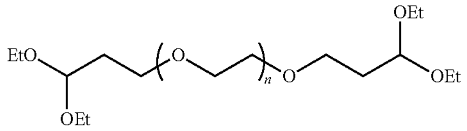

Formula 3

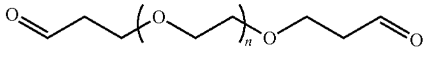

wherein n may be a natural number from 30 to 115.

In the composition, the content ratio of the polyethylene glycol derivative represented by Formula 1A within a range of the number average molecular weight of 2950 to 3650 is at least 70 area % based on high performance liquid chromatography (HPLC), the content ratio of the polyethylene glycol derivative represented by Formula 2 within a range of the number average molecular weight of 2950 to 3650 is 15 area % or less based on HPLC, and the content ratio of the polyethylene glycol derivative represented by Formula 3 within a range of the number average molecular weight of 2950 to 3650 is 10 area % or less based on HPLC.

The number average molecular weight of the polyethylene glycol derivatives in the composition may be in the range of 2950 to 3650, the measurements obtained by gel permeation chromatography.

The number average molecular weight of the polyethylene glycol derivatives in the composition may be in the range of 3000 to 3200, the measurements obtained by gel permeation chromatography.

A method for producing a physiologically active polypeptide conjugate according to an aspect includes:

(a) a pegylation process in which a polyethylene glycol derivative compound of Formula 1 is reacted with a physiologically active polypeptide to generate a linkage in which the physiologically active polypeptide is covalently conjugated with the aldehyde carbon of the polyethylene glycol derivative compound of Formula 1;

(b) a hydrolysis process in which the linkage is treated in an acidic aqueous condition to form a linkage hydrolyzate; and (c) a conjugation process in which the linkage hydrolyzate is reacted with an immunoglobulin Fc fragment or a derivative thereof to generate a conjugate.

Formula 1

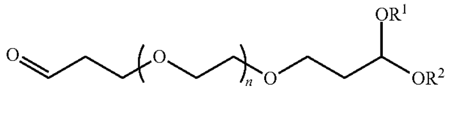

In Formula 1, n may be a natural number of 50 to 100, and $R^1$ and $R^2$ may be $C_1$ to $C_5$ alkyl that are identical to or different from each other.

The conjugate has a structure in which the Fc fragment or the derivative thereof is covalently conjugated with a carbon atom derived from the acetal carbon of the polyethylene glycol derivative compound of Formula 1 in the linkage hydrolyzate.

The physiologically active polypeptide may be selected from hormones, cytokines, enzymes, antibodies, growth factors, transcriptional regulators, blood coagulation factors, vaccines, structural proteins, ligand proteins, and receptors.

The reaction of process (a) is a reductive amination,

The linkage may be a material in which the N-terminal nitrogen of the physiologically active polypeptide or the nitrogen atom of the ε-amino group of lysine is covalently conjugated with the aldehyde carbon atom of the polyethylene glycol derivative compound of Formula 1.

The pegylation reaction of process (a) may be carried out at the pH of 3.0 to 9.0.

The hydrolysis of process (b) may be carried out at the pH of 1.0 to 5.0.

The conjugation reaction in process (c) may be reductive amination.

The reductive amination may be carried out at the pH of 5.0 to 8.5.

The sequence of the Fc fragment or derivative thereof at N-terminus may be a proline.

In the conjugate, the nitrogen atom of the N-terminal proline of the Fc fragment or derivative thereof may be covalently conjugated with a carbon atom derived from the acetal carbon.

The Fc fragment or derivative thereof may have the amino acid sequence of SEQ ID NO: 2.

$R^1$ and $R^2$ may each be ethyl.

n may be a natural number from 67 to 83.

Advantageous Effects of Disclosure

A physiologically active polypeptide conjugate can be prepared in high yields by binding a physiologically active polypeptide and an Fc fragment or a derivative thereof to a polyethylene glycol derivative having a reactive aldehyde group at one end and an unreactive acetal group at the other end.

BEST MODE

Figure 1:
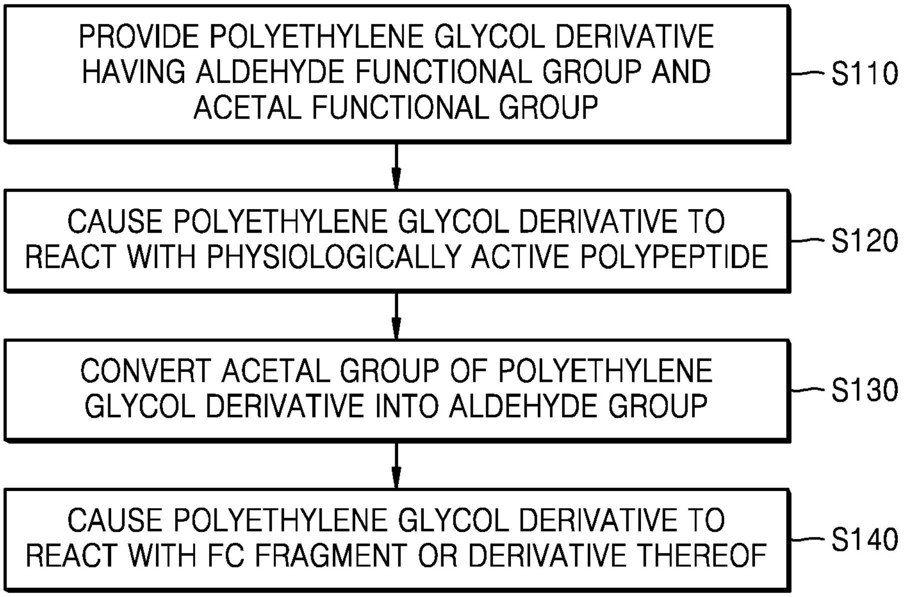
FIG. 1 shows a flowchart illustrating a method of preparing a physiologically active polypeptide conjugate according to an embodiment.

Hereinafter, the present disclosure will be described in detail.

All technical terms used in the present disclosure have the meanings commonly understood by those of ordinary skill in the art, unless defined otherwise. In addition, although preferred methods and samples are described herein, similar or equivalent methods sand samples are also included in the scope of the present disclosure. In addition, the numerical values described herein are considered to include the meaning of 'about' even if not specified. The contents of all publications incorporated herein by reference are hereby incorporated by reference in their entirety.

A polyethylene glycol derivative according to an aspect of the present disclosure will be described.

The polyethylene glycol derivative has an aldehyde group (ALD) at one end of polyethylene glycol (PEG) and an acetal group (ACT) at the other end thereof. The polyethylene glycol derivative may be represented by General Formula 1.

ALD-PEG-ACT General Formula 1 In General Formula 1, ALD is an aldehyde functional group, PEG is a polyethylene glycol moiety, and ACT is an acetal group.

The PEG moiety in General Formula 1 may be represented by $(—O—C_2H_4)_n—O—$, wherein n may be 30 to 115 or 50 to 100. In an embodiment, n may range from 67 to 83. The PEG binds to a physiologically active polypeptide and an Fc fragment or a derivative thereof to increase the in vivo half-life of the physiologically active polypeptide, and may transport the physiologically active polypeptide into the body.

The ALD group may be a reactive functional group, and may be an alkyl aldehyde, such as a $C_2$-$C_6$ alkyl aldehyde. The ALD group may be a propion aldehyde group, a butyl aldehyde group, or the like, but is not particularly limited thereto. The ALD group may react with the physiologically active polypeptide to bind the physiologically active polypeptide to PEG. In an embodiment, the ALD group may react with the Fc fragment or derivative thereof to bind the Fc fragment or derivative thereof to PEG.

The ACT group is an unreactive functional group and does not react with the physiologically active polypeptide or a Fc fragment or derivative thereof. Therefore, while one end of PEG is bound to a physiologically active polypeptide or a Fc fragment or derivative thereof through the reaction of the ALD group, the other end of PEG may be protected by the ACT group, which is an unreactive functional group.

The ACT group may be represented by $—R_1CH(OR_2)(OR_3)$, and $R_1$ to $R_3$ may each independently be a $C_2$-$C_6$ alkyl group. The acetal group (ACT) may be a 1,1-diethoxy propyl group, a 1,1-diethoxy butyl group, and the like, but is not limited thereto.

Meanwhile, the ACT group may be hydrolyzed to an aldehyde group to form a second ALD group. The second ALD group may react with a physiologically active polypeptide or a Fc fragment or derivative thereof to bind the physiologically active polypeptide or a Fc fragment or derivative thereof to the other end of PEG.

An example of the polyethylene glycol derivative of General Formula 1 may be represented by Formula 1:

Formula 1

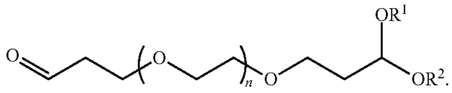

$R^1$ and $R^2$ in Formula 1 may be $C_1$ to $C_5$ alkyl groups which are identical to or different from each other. In this case, the $C_1$ to $C_5$ alkyl groups may include a linear, branched or cyclic alkyl group. The $C_1$ to $C_5$ alkyl may be, for example, methyl, ethyl, propyl, or butyl. $R^1$ and $R^2$ may be, for example, ethyl groups.

n may range from 30 to 115. In an embodiment, n may range from 50 to 100. In an embodiment, n may range from 67 to 83. The acetal group of Formula 1 may be hydrolyzed during the formation of a physiologically active peptide conjugate to be converted into a second aldehyde group.

Specifically, the polyethylene glycol derivative of Formula 1 may be represented by Formula 1A.

Formula 1A

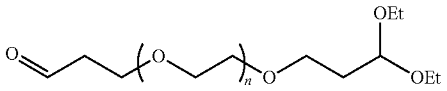

n is the same as n in Formula 1.

A polyethylene glycol derivative composition according to another aspect of the present disclosure will be described.

The polyethylene glycol derivative may form a composition containing impurities. The impurities may include a polyethylene glycol derivative in which both ends of polyethylene glycol are acetal groups and/or a polyethylene glycol derivative in which both ends of polyethylene glycol are aldehyde groups. The content ratio of the polyethylene glycol derivative having an aldehyde group at one end thereof and an acetal group at the other end in the composition may be considered as the purity of the polyethylene glycol derivative having an aldehyde group at one end thereof and an acetal group at the other end. The amount of these impurities may be calculated as the area % of the corresponding peak measured by high performance liquid chromatography (HPLC).

In an embodiment, a polyethylene glycol derivative composition according to an aspect may include:

- a polyethylene glycol derivative represented by Formula 1A;
- a polyethylene glycol derivative represented by Formula 2; and
- a polyethylene glycol derivative represented by Formula 3:

Formula 1A

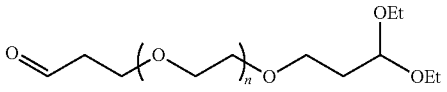

Formula 2

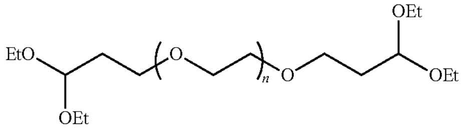

-continued

Formula 3

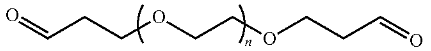

n in Formulae 1A, 2, and 3 may be a natural number of 30 to 115.

In the composition, the polyethylene glycol derivative represented by Formula 1A may have a number average molecular weight within the range of 2950 to 3650, and may have the content ratio of at least 75 area % based on HPLC.

The polyethylene glycol derivative represented by Formula 2 may have the number average molecular weight of 2950 to 3650, and may have the content ratio of 15 area % or less based on HPLC.

The polyethylene glycol derivative represented by Formula 3 may have the number average molecular weight of 2950 to 3650, and may have a content ratio of 10 area % or less based on HPLC.

The number average molecular weight of the polyethylene glycol derivatives in the composition may be a value measured by gel permeation chromatography.

The number average molecular weight of the polyethylene glycol derivatives in the composition may be in the range of 3000 to 3200, the measurements obtained by gel permeation chromatography.

The number average molecular weight of a compound may be measured by gel permeation chromatography.

A method of preparing a physiologically active polypeptide conjugate according to another aspect of the present disclosure will be described. FIG. 1 shows a flowchart illustrating a method of preparing a physiologically active polypeptide conjugate according to an embodiment.

Referring to FIG. 1, according to the method of preparing the physiologically active polypeptide conjugate, a polyethylene glycol derivative comprising PEG having an aldehyde functional group at one end thereof and an acetal functional group at the other end (S110). The polyethylene glycol derivative is a compound represented by General Formula 1, Formula 1 or Formula 1A, and the afore description of the compound of General Formula 1, Formula 1 or Formula 1A may be applicable in the following embodiments.

Then, the polyethylene glycol derivative is reacted with the physiologically active polypeptide (S120). Through this reaction, a linkage in which the physiologically active polypeptide is covalently conjugated with the aldehyde carbon of the polyethylene glycol derivative may be formed. This linkage formation reaction may be a pegylation reaction. This pegylation reaction may be a reductive amination reaction. The pegylation reaction may be carried out at the pH of 3.0 to 9.0, for example, at the pH of 5.0 to 9.0.

The physiologically active polypeptide may comprise, for example, a hormone, a cytokine, an enzyme, an antibody, a growth factor, a transcriptional regulator, a blood coagulation factor, a vaccine, a structural protein, a ligand protein, or a receptor. For example, the physiologically active polypeptide may be exendin-4 or imidazoacetyl exendin-4. In an embodiment, the linkage may be a material in which the N-terminal nitrogen of the physiologically active polypeptide or the nitrogen atom of the ε-amino group of lysine is covalently conjugated with the aldehyde carbon atom of the compound of Formula 1.

Then, the acetal group of the other end of the polyethylene glycol derivative of which one end is bonded to the physiologically active polypeptide may be converted into an aldehyde group (S130).

For example, an acetal group may be converted to an aldehyde group by hydrolysis. In this case, the hydrolysis may be carried out in, for example, an acidic aqueous condition. The hydrolysis may be performed at the pH of 1.0 to 5.0, for example, at the pH of 2.0 to 5.0. When $R^1$ and/or $R^2$ of the acetal group of Formula 1 is a propyl group, the aldehyde group formed by hydrolysis may be a propion aldehyde group.

Subsequently, the converted aldehyde group of the polyethylene glycol derivative may be reacted with the Fc fragment or the derivative thereof (S140). By the reaction, the other end of the polyethylene glycol derivative may be conjugated with the Fc fragment or the derivative thereof. In this case, Fc fragment or the derivative thereof may be covalently conjugated with a carbon atom derived from the carbon of the acetal group.

For example, in the case where the polyethylene glycol derivative is the polyethylene glycol derivative compound represented by Formula 1, the aldehyde group of the physiologically active polypeptide may be reacted with the physiologically active polypeptide to bind the physiologically active polypeptide to the end of the polyethylene glycol derivative. In this regard, a pegylation reaction may occur between the physiologically active polypeptide and the aldehyde group. The pegylation reaction may use, for example, a reductive amination. Subsequently, the ACT group which is a functional group remaining unreacted in the polyethylene glycol derivative-physiologically active polypeptide linkage obtained in this way, may be hydrolyzed and converted into a second reactive aldehyde group. The converted second aldehyde group of this polyethylene glycol derivative-physiologically active polypeptide linkage may be reacted with the Fc fragment or the derivative thereof. This reaction is a conjugation reaction, and may use, for example, a reductive amination reaction. The reductive amination may be carried out at the pH of 5.0 to 8.5. Due to this reaction, the Fc fragment or the derivative thereof may be bound to the other end of the polyethylene glycol derivative-physiologically active polypeptide linkage. As such, formed is a physiologically active polypeptide conjugate in which one end of the polyethylene glycol derivative may be conjugated with a physiologically active polypeptide, and the other end may be conjugated with the Fc fragment or the derivative thereof. The conjugate may be, for example, a conjugate in which the nitrogen atom of the N-terminal proline of the Fc fragment or derivative thereof is covalently conjugated with a carbon atom derived from the acetal carbon of the polyethylene glycol derivative. An acetyl carbon is a carbon to which an —OR group is linked.

The method of producing a physiologically active polypeptide conjugate using polyethylene glycol derivatives according to embodiments of the present disclosure provides high yield while suppressing the generation of impurities or related substances.

In the process (pegylation) of conjugating a polyethylene glycol derivative having a functional group at an end thereof with a physiologically active polypeptide, a related substance intermediate in which two or more units of polyethylene glycol derivative are conjugated with one unit of physiologically active polypeptide may inevitably be produced. When the molecular weight of polyethylene glycol derivative is not large, conventional chromatography is not enough to completely purify and filter these related substance intermediates before entering the subsequent conjugation reaction.

In the case of using the polyethylene glycol derivative of the prior art having an aldehyde functional group at both ends thereof, the remaining related substance intermediate reacts with the Fc fragment in the subsequent conjugation process to cause the formation of impurities in the form of multimers (dimers, trimers, etc.). In addition, in the production using polyethylene glycol derivatives of the prior art, a sandwich-structured polyethylene glycol linkage, such as a physiologically active polypeptide-polyethylene glycol derivative-physiologically active polypeptide, may be generated during the pegylation process. Due to these reaction by-products, the yield may be reduced.

In the case of using the polyethylene glycol derivative of the prior art having an aldehyde functional group at both ends thereof, due to the high reactivity of the aldehyde group, the aldehyde group may first react with a substance other than the reaction target and be thus lost. In addition, in the process of producing the polyethylene glycol derivative, the terminal group thereof may be modified. Accordingly, the polyethylene glycol derivative itself may have a certain level of impurities. When an aldehyde group at an end is converted into a hydroxyl group or an ether group due to the loss of the activity or modification of the aldehyde group, and a related substance having a single aldehyde group undergoes a pegylation reaction, a polyethylene glycol linkage having a corresponding structure may be generated. This polyethylene glycol linkage does not lead to a final conjugate because there is no aldehyde group capable of reacting with Fc fragment or the derivative thereof by a subsequent conjugation reaction. Therefore, the generation of a related substance having such a single aldehyde group may cause impurities in the method of preparing conjugates of the prior art and a decrease in the yield.

When the polyethylene glycol derivative according to the embodiment of the present disclosure is used for the preparation of a physiologically active polypeptide conjugate, the generation of such impurities may be fundamentally prevented. Unlike the polyethylene glycol derivatives of the prior art, the polyethylene glycol derivatives according to the embodiment of the present disclosure contain an aldehyde group only at one end thereof. Accordingly, a multimer fundamentally cannot be formed. In addition, in the preparation method using a polyethylene glycol derivative according to the embodiment of the present disclosure, when the aldehyde group is lost or changed to a related substance before pegylation, a physiologically active polypeptide-polyethylene glycol linkage, which is a pegylation product, may not be generated from the beginning. Therefore, the generation of related substances may be suppressed and purification is simplified, which leads to an improvement in the yield of the pegylation process. Furthermore, as to be described later, the efficiency of the conjugation reaction step after pegylation is also higher than that of the prior art, and the purity in the purification process is improved.

With regard to these advantages, a general comparison will be made between the yields of the process of the present disclosure and that of the prior art. First, in a specific embodiment of the present disclosure, the aldehyde activity (the degree to which the aldehyde group is maintained until immediately before the conjugation reaction) of the physiologically active polypeptide-polyethylene glycol linkage, which is a pegylation product, is usually at the level of 80% to 95%. This is significantly higher than the aldehyde activity of the linkage using a polyethylene glycol derivative of the prior art, which is 60% to 75%. In addition, in the preparation method of the present disclosure, since the yield of the conjugation process is also increased, the final yield of the physiologically active polypeptide conjugate in a specific embodiment of the present disclosure is generally increased to about 1.2 times to about 1.7 times the level of the production method of the prior art.

MODE OF DISCLOSURE

Hereinafter, a specific embodiment for the preparation of the physiologically active polypeptide conjugate of the present disclosure will be described.

First, polyethylene glycol derivative (ALD-PEG-DEP) was prepared in which both ends of the ethylene glycol repeating unit were modified with a propylaldehyde group and a 3-diethoxypropyl group, respectively.

Experimental Example 1: Preparation of ALD-PEG-DEP 1

(a) Preparation of PEG-mesylate (Ms)

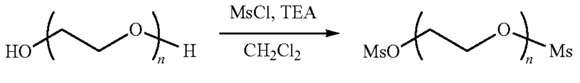

PEG 3.4K PEG-Ms

A solution obtained by dissolving 100 g of PEG (number average molecular weight of 3400) in 300 mL of dichloromethane ($CH_2Cl_2$) in a reactor in a nitrogen atmosphere was cooled to 5° C. 23.0 mL of triethylamine (TEA) was added to this solution, and 12.6 mL of methanesulfonyl chloride (MsCl) was added thereto while the temperature was maintained at 5° C. After the reaction solution was stirred at 5° C. for 2.5 hours, 300 mL of distilled water was added thereto, and stirred for 10 minutes. Then, the organic layer was separated therefrom.

300 mL of dichloromethane was added to the aqueous layer to further extract the organic layer, and then this organic layer was combined with the organic layer which had been previously separated. The combined organic layers were washed with distilled water, dried over anhydrous magnesium sulfate, and filtered. After the filtrate was concentrated under reduced pressure, the concentrated solution was dissolved in 100 mL of dichloromethane and then added dropwise to 1500 mL of methyl t-butyl ether for 30 minutes. After the reaction solution was stirred at room temperature for 1 hour, the solid was filtered. Then, the solid was washed with methyl t-butyl ether, and then dried with nitrogen at room temperature to obtain 97 g of the target compound, PEG-Ms (yield: 92.6%).

(b) Preparation of PEG-DEP

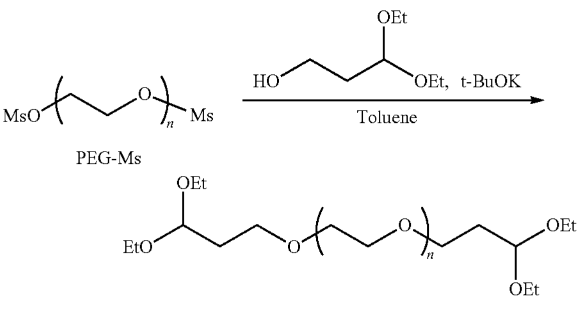

PEG-Ms

PEG -DEP 1.8 mL of 3,3-diethoxy-1-propanol and 40 mL of toluene were added to a first reactor in a nitrogen atmosphere. 1.4 g of potassium t-butoxide (t-BuOK) was added thereto, the temperature was raised to 50° C., and the resultant mixture was stirred for 1 hour. The reaction solution was cooled to room temperature.

In a nitrogen atmosphere, 10 g of PEG-Ms prepared as described above and 40 mL of toluene were added to a second reactor. The activated solution of the first reactor was slowly added dropwise thereto for 1 hour. After the resultant mixture was stirred at room temperature for 2 hours and the reaction was completed, a saturated aqueous solution of ammonium chloride was added to the reaction product. After the reaction product was stirred for 5 minutes, dichloromethane was added to extract the organic layer. The organic layer was further extracted by adding dichloromethane to the aqueous layer. The organic layers were combined, concentrated under reduced pressure, completely dissolved in 10 mL of dichloromethane, and crystallized by dropwise addition of methyl t-butyl ether. After the resultant mixture was stirred at room temperature for 2 hours, the crystals were filtered and washed with methyl t-butyl ether. The crystals were nitrogen-dried at room temperature to obtain 9.3 g (yield: 90.0%) of the target compound, PEG-diethyl acetal (PEG-DEP).

(c) Preparation of ALD-PEG-DEP

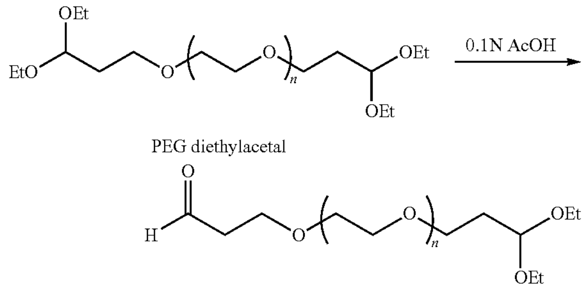

PEG diethylacetal

ALD-PEG-DEP 360 mL of 0.1 N acetic acid and 60 g of PEG-DEP were added and dissolved in a reactor, followed by stirring at 20° C. for 4 hours. To this solution, a 5% aqueous sodium hydrogen carbonate solution and distilled water were added, followed by stirring for 5 minutes. After adding dichloromethane and hexane to the reaction solution and stirring for 10 minutes, the aqueous layer was separated therefrom. After adding dichloromethane and hexane to the aqueous layer and stirring for 10 minutes, the organic layer was separated. The organic layers were combined, dried over magnesium sulfate, filtered, and concentrated under reduced pressure. Dichloromethane was added thereto to dissolve the concentrate, and then, methyl t-butyl ether was added dropwise thereto to cause crystallization. After the resultant mixture was stirred at room temperature for 30 minutes, the crystals were filtered and washed with methyl t-butyl ether. The crystals were nitrogen-dried with at room temperature to obtain the target compound. The target compound was a 3.4 kDa ALD-PEG-DEP, a polyethylene glycol derivative in which both ends of a 3.4 kDa ethylene glycol repeating unit were modified with a propylaldehyde group and a 3-diethoxypropyl group, respectively, and the production amount was 16.0 g (yield: 26.7%). The number average molecular weight measured by gel permeation chromatography (GPC) was 3111.

Experimental Example 2: Preparation of ALD-PEG-DEP 2

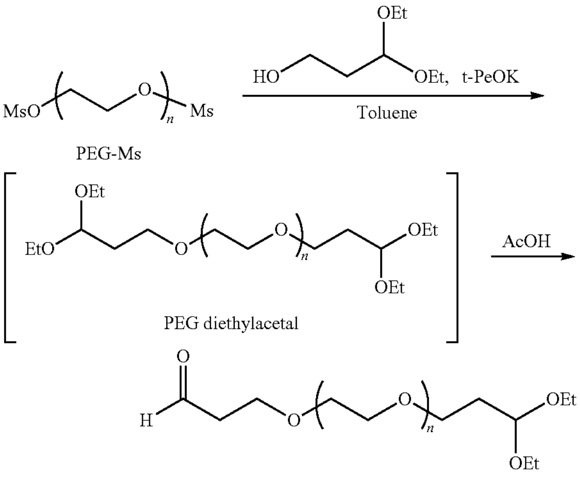

PEG-Ms

PEG diethylacetal

ALD-PEG-DEP (a) Preparation of PEG-Ms

PEG-Ms were prepared in the same manner as in the preparation method of PEG-Ms of Experimental Example 1.

(b) Preparation of ALD-PEG-DEP 45 mL of 3,3-diethoxy-1-propanol and 400 mL of toluene were added to a first reactor in a nitrogen atmosphere. 15.7 g of potassium t-pentoxide (t-PeOK) was added thereto, the temperature was raised to 50° C., and the resultant mixture was stirred for 1 hour. The reaction solution was cooled to room temperature.

In a nitrogen atmosphere, 100 g of PEG-Ms prepared as described above and 400 mL of toluene were added to a second reactor. The activated solution of the first reactor was slowly added dropwise thereto for 1 hour. After the resultant mixture was stirred at room temperature for 2.5 hours and the reaction was completed, distilled water was added to the reaction product. After stirring the reaction product for 5 minutes, the aqueous layer was separated. Dichloromethane and toluene were added to the aqueous layer to extract the organic layer. Distilled water was added to the organic layer and stirred for 5 minutes, and then, the aqueous layer was further separated.

13 mL of acetic acid was added to the separated aqueous layer and stirred at room temperature for 2.5 hours. A 5% aqueous sodium hydrogen carbonate solution was added thereto, followed by stirring for 5 minutes. Dichloromethane and hexane were mixed in a third reactor, and then, the previous reaction solution was added thereto. The mixed solution was stirred for 10 minutes, and then, the aqueous layer was separated therefrom. To the separated aqueous layer, 5% aqueous sodium hydrogen carbonate solution was added and stirred for 5 minutes. Dichloromethane and hexane were mixed in a third reactor, and then, the reaction solution was added and stirred for 10 minutes. Then, the organic layer was separated therefrom. Distilled water was added to the separated organic layer and stirred, and the organic layer was separated therefrom. The organic layer was dried over magnesium sulfate, filtered, and concentrated under reduced pressure. Dichloromethane was added thereto to dissolve the concentrate, and then, methyl t-butyl ether was added dropwise thereto to cause crystallization. After the resultant mixture was stirred at room temperature for 30 minutes, the crystals were filtered and washed with methyl t-butyl ether. The crystals were nitrogen-dried at room temperature to obtain 10.1 g (yield: 10.1%) of the target compound, 3.4 kDa ALD-PEG-DEP. The number average molecular weight measured by gel permeation chromatography was 3163.

Analysis Example: Comparison of Properties of ALD-PEG-DEP and ALD-PEG-ALD

Properties of ALD-PEG-DEP, a polyethylene glycol derivative prepared according to the method according to an embodiment of the present disclosure, and ALD-PEG-ALD, a commercially available polyethylene glycol derivative modified with propylaldehyde groups at both ends thereof (manufactured by Hanmi Fine Chemical Corporation, Korea, the chemical formula weight of the ethylene glycol repeating unit was 3.4 kDa), were measured and the obtained results were compared. For this purpose, MALDI-TOF mass spectrometry, nuclear magnetic resonance analysis (1H NMR, 13C NMR) and Fourier transform infrared spectroscopy (FT-IR) were performed.

Figure 2A:
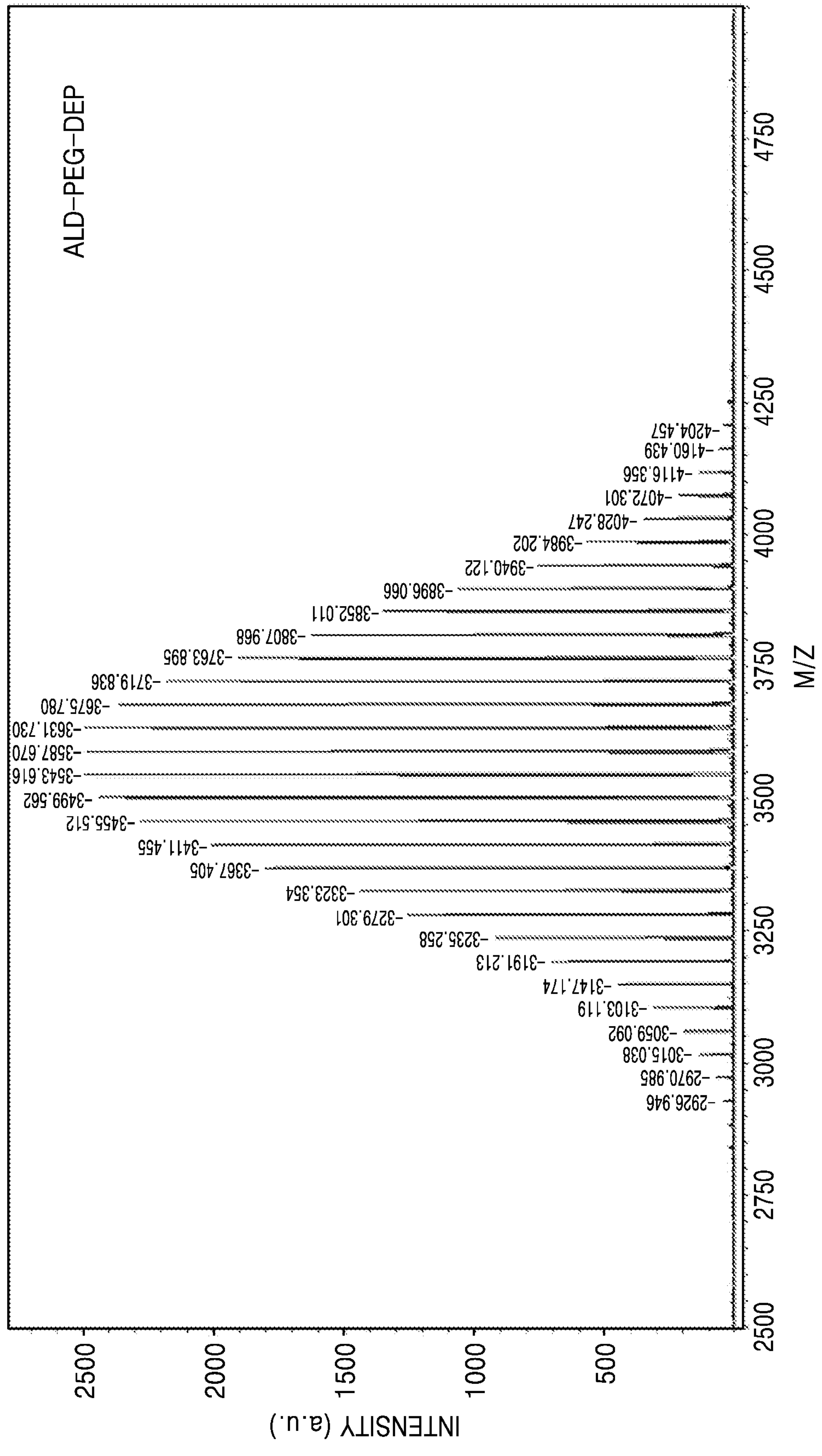
FIGS. 2A and 2B are MALDI-TOF mass spectrometry graphs of aldehyde (ALD)-PEG-diethoxypropyl (DEP) prepared in Experimental Example 2 and commercially available ALD-PEG-ALD, respectively.
Figure 2B:
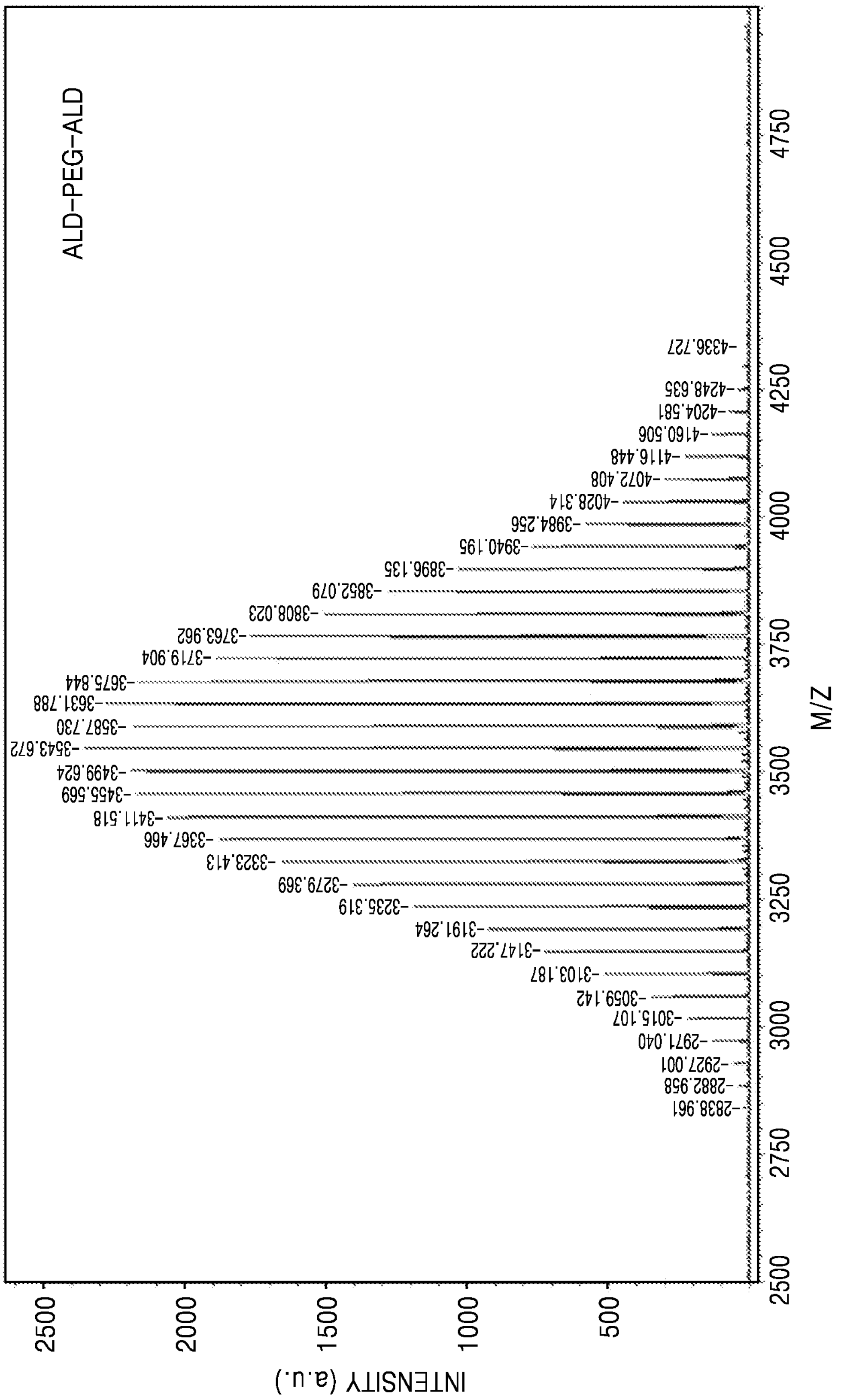

FIGS. 2A and 2B show MALDI-TOF mass spectrometry graphs of ALD-PEG-DEP prepared in Experimental Example 2 and commercially available ALD-PEG-ALD, respectively. Table 1 show molecular weights of ALD-PEG-DEP prepared in Experimental Example 2 and commercially available ALD-PEG-ALD.

TABLE 1

| Molecular Weight | ALD-PEG-DEP | ALD-PEG-ALD |
|---|---|---|
| Mn | 3538.8 | 3520.7 |
| Mw | 3551.8 | 3536.4 |
| Mw/Mn | 1.00 | 1.00 |

Figure 3A:
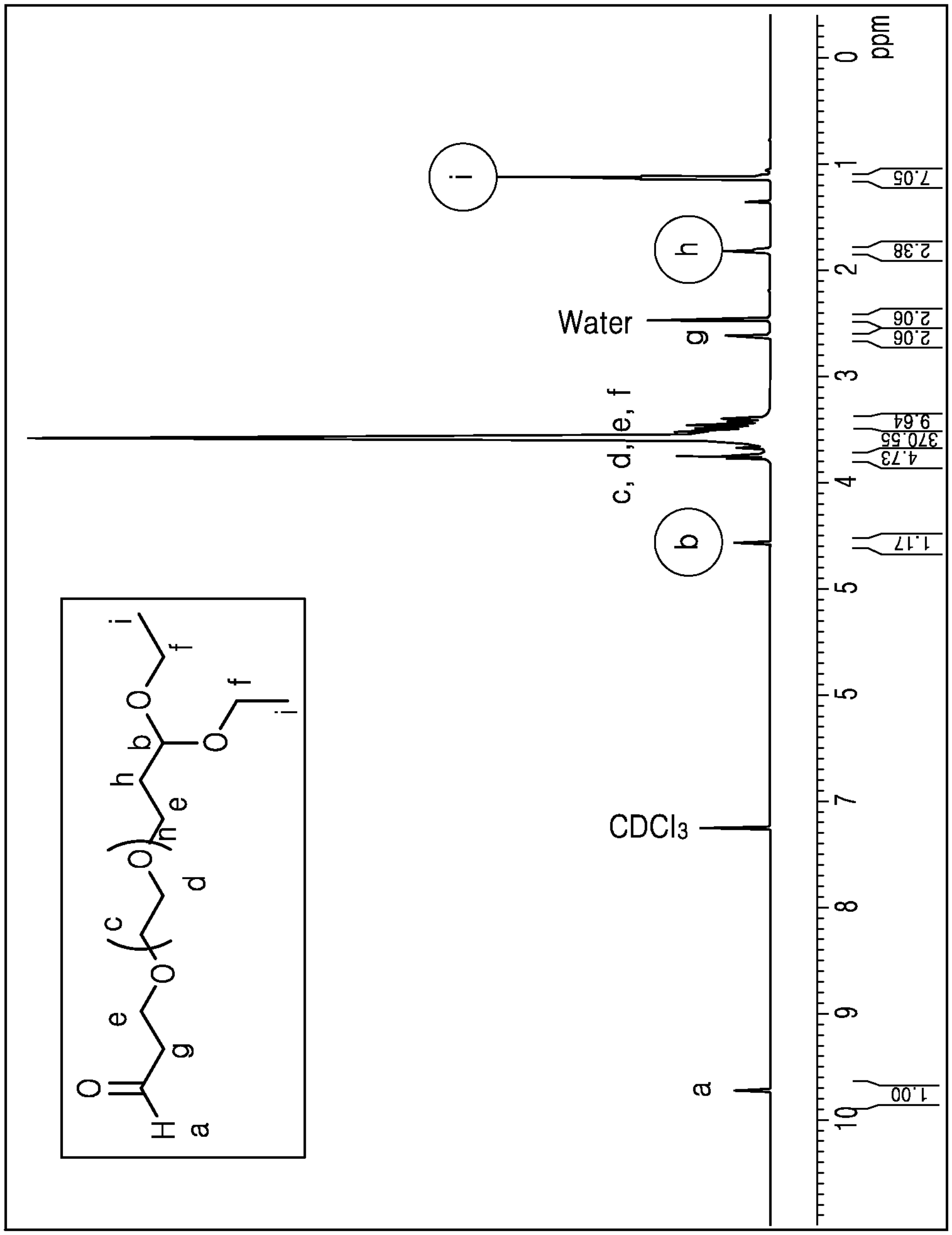
FIGS. 3A and 3B show graphs of nuclear magnetic resonance (1H NMR) spectra of ALD-PEG-DEP of Experimental Example 2 and commercially available ALD-PEG-ALD, respectively.
Figure 3B:
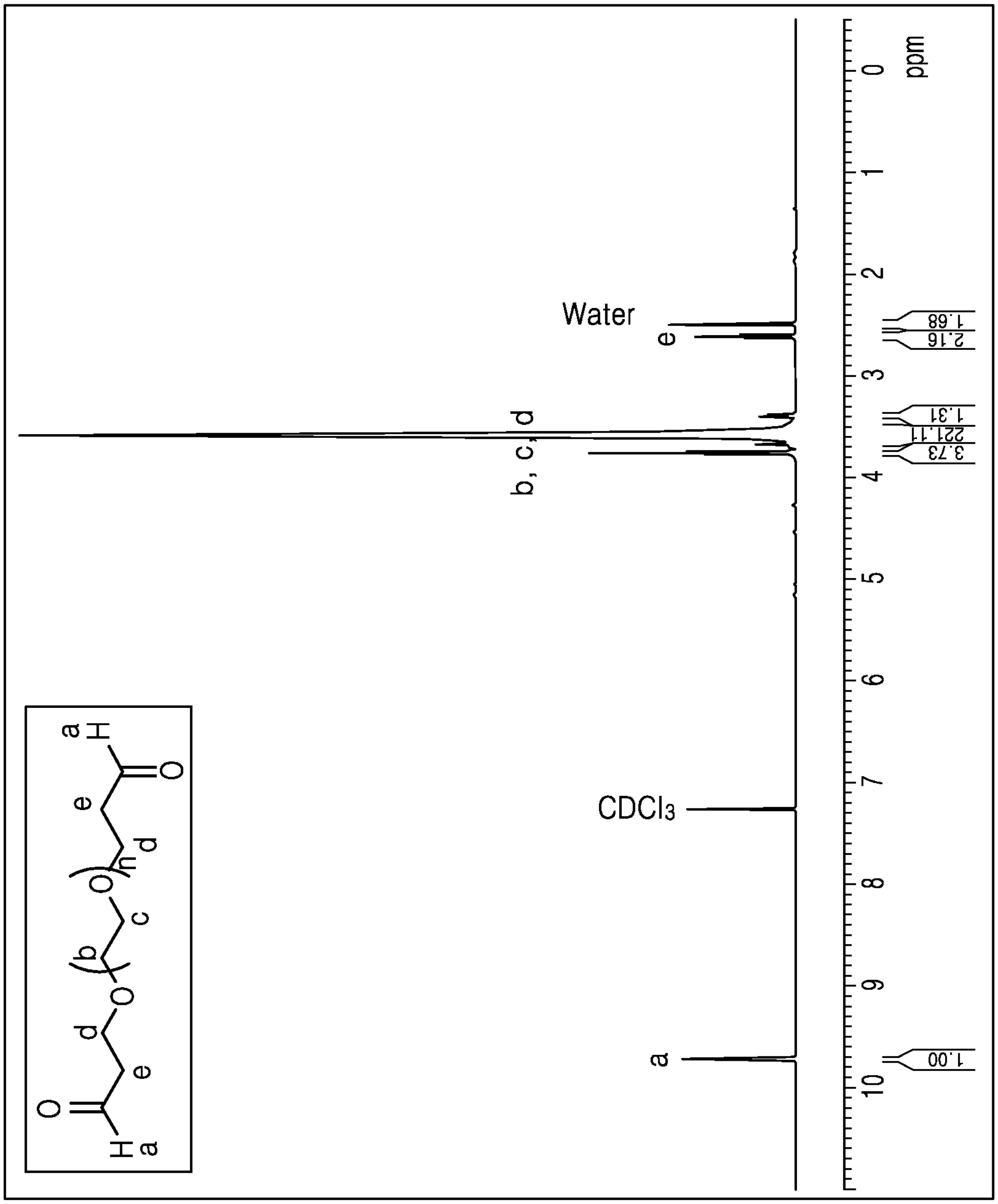

Referring to FIGS. 2A, 2B and Table 1, it can be seen that there is no significant difference in molecular weights of ALD-PEG-DEP of Experimental Example 2 and the commercially available ALD-PEG-ALD. FIGS. 3A and 3B show graphs of nuclear magnetic resonance (1H NMR) spectra of ALD-PEG-DEP of Experimental Example 2 and commercially available ALD-PEG-ALD, respectively. In the 1H-NMR spectrum of FIGS. 3A and 3B, peaks corresponding to the diethoxy group (triplet (b) around 4.6 ppm and 1.2 ppm (i), and multiplet (h) around 1.8 ppm) show that the ALD-PEG-DEP of the Experimental Example has an acetal end group. On the other hand, peaks corresponding to the diethoxy group do not appear in the 1H-NMR spectrum of FIG. 2B.

Figure 3C:
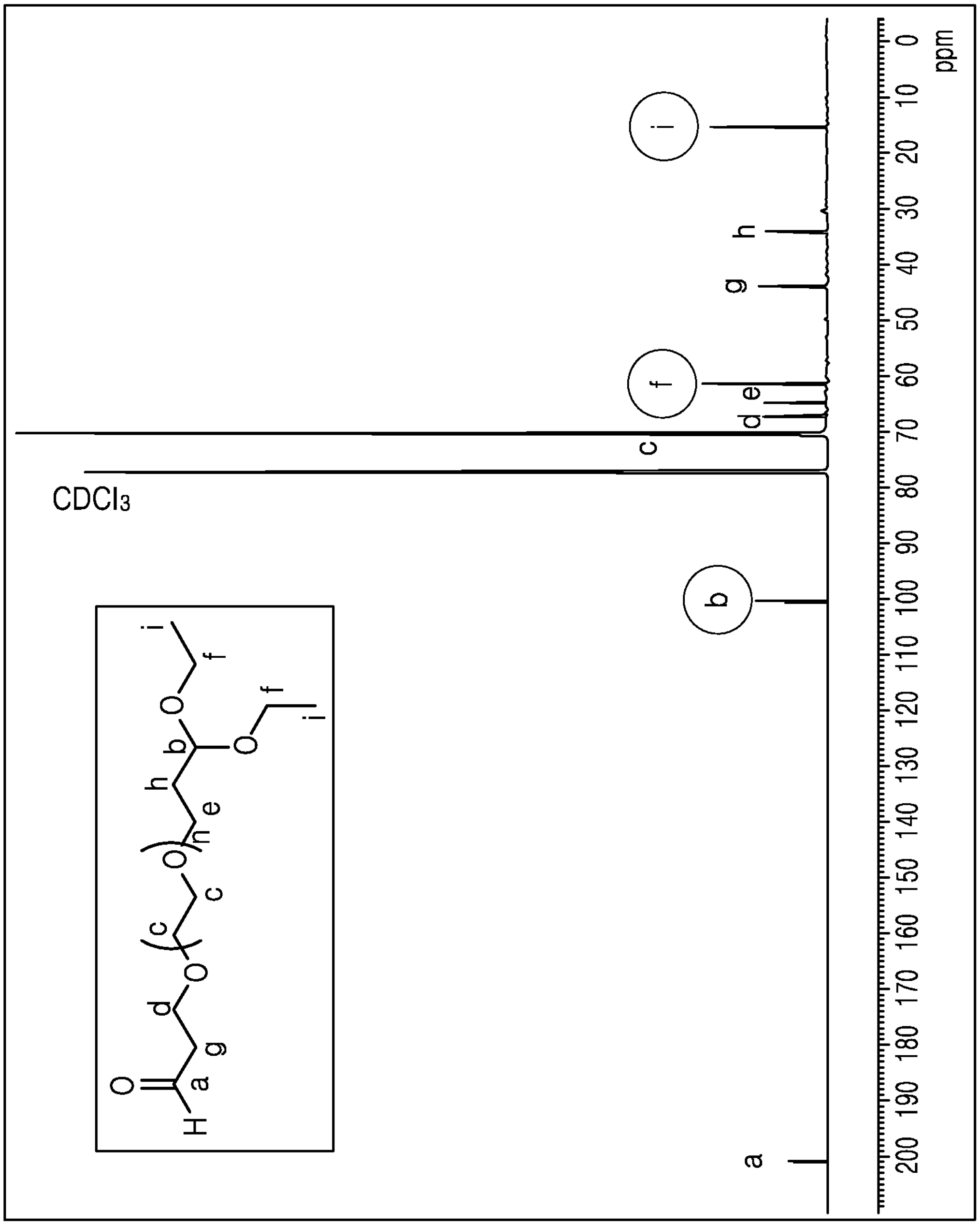
FIGS. 3C and 3D show graphs of nuclear magnetic resonance (13C NMR) spectra of ALD-PEG-DEP of Experimental Example 2 and commercially available ALD-PEG-ALD, respectively.
Figure 3D:
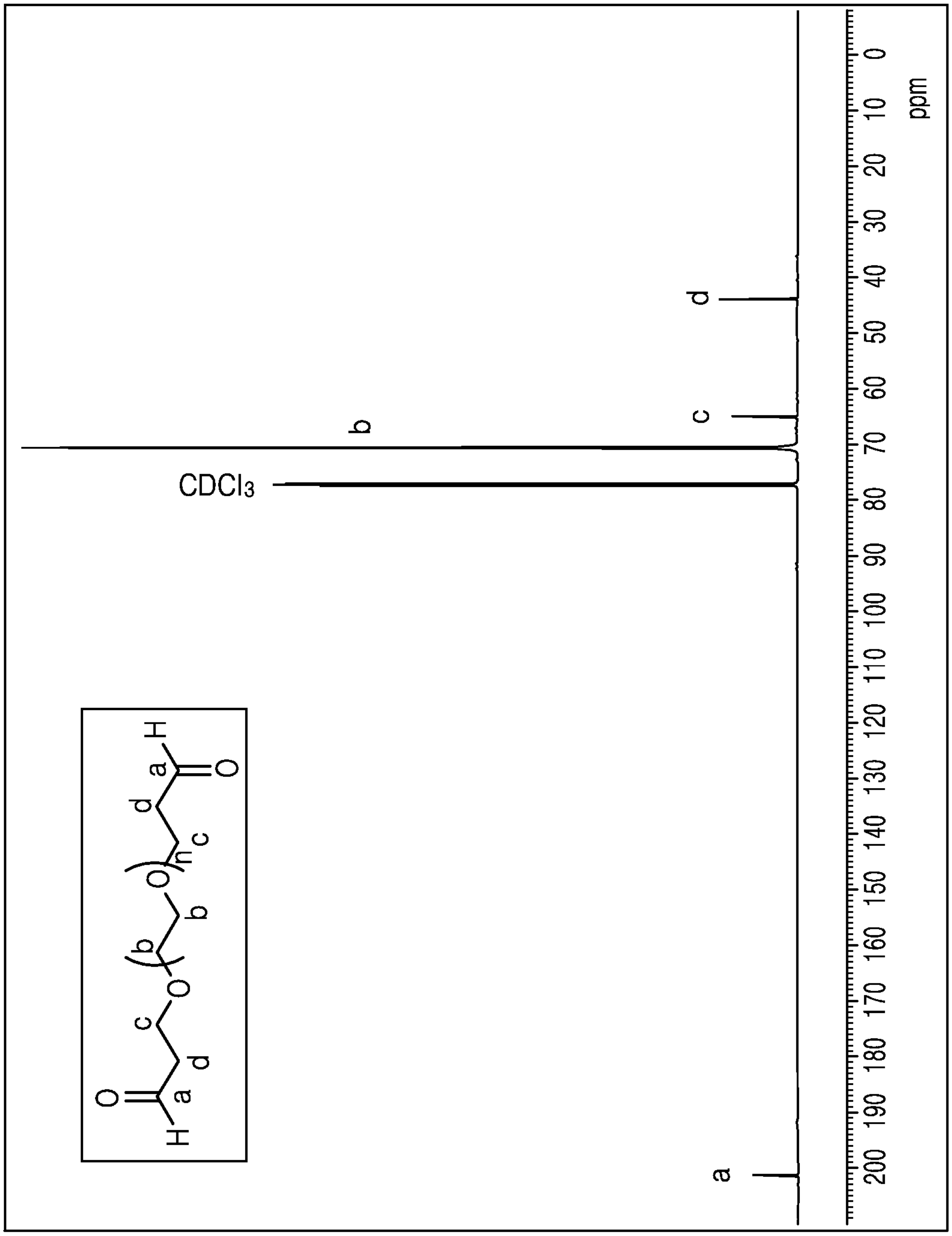

FIGS. 3C and 3D show graphs of nuclear magnetic resonance (13C NMR) spectra of ALD-PEG-DEP of Experimental Example 2 and commercially available ALD-PEG-ALD, respectively. In the 13C-NMR spectrum of FIG. 3C, a peak corresponding to an ethyl group appeared at δ 15 ppm (i) and 62 ppm (f) and a peak of secondary carbon appeared at δ 101 ppm (b). The graph of FIG. 3C had peaks of ALD-PEG-DEP having asymmetric molecular structure, and the graph of FIG. 3D had peaks of ALD-PEG-ALD having a symmetric molecular structure (peaks (e) and (f) of ALD-PEG-DEP vs peak (c) of ALD-PEG-ALD (c); peaks (h) and (i) of ALD-PEG-DEP vs peak (d) of ALD-PEG-ALD).

Figure 4A:
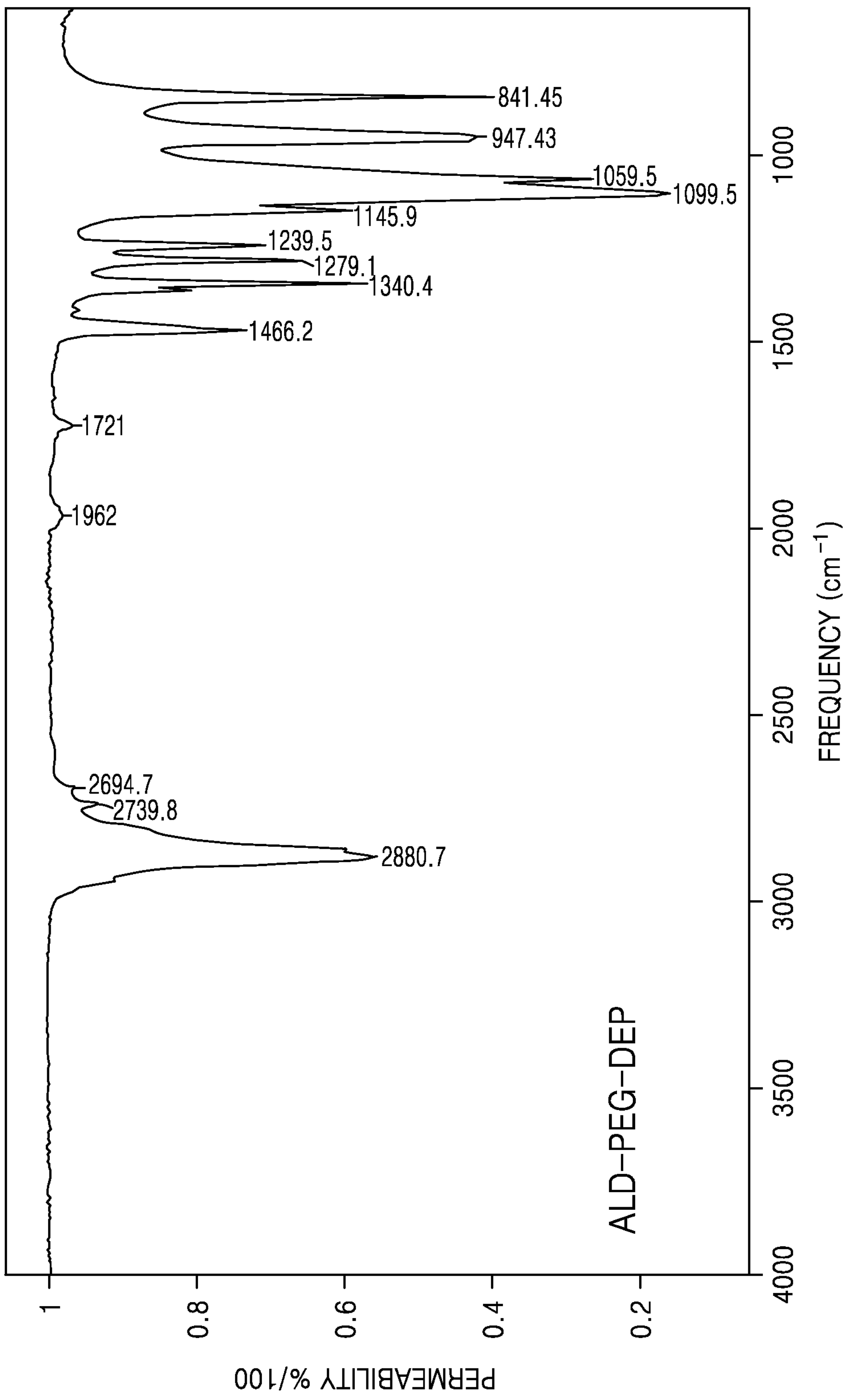
FIGS. 4A and 4B show FT-IR spectra of ALD-PEG-DEP of Experimental Example 2 and commercially available ALD-PEG-ALD, respectively.
Figure 4B:
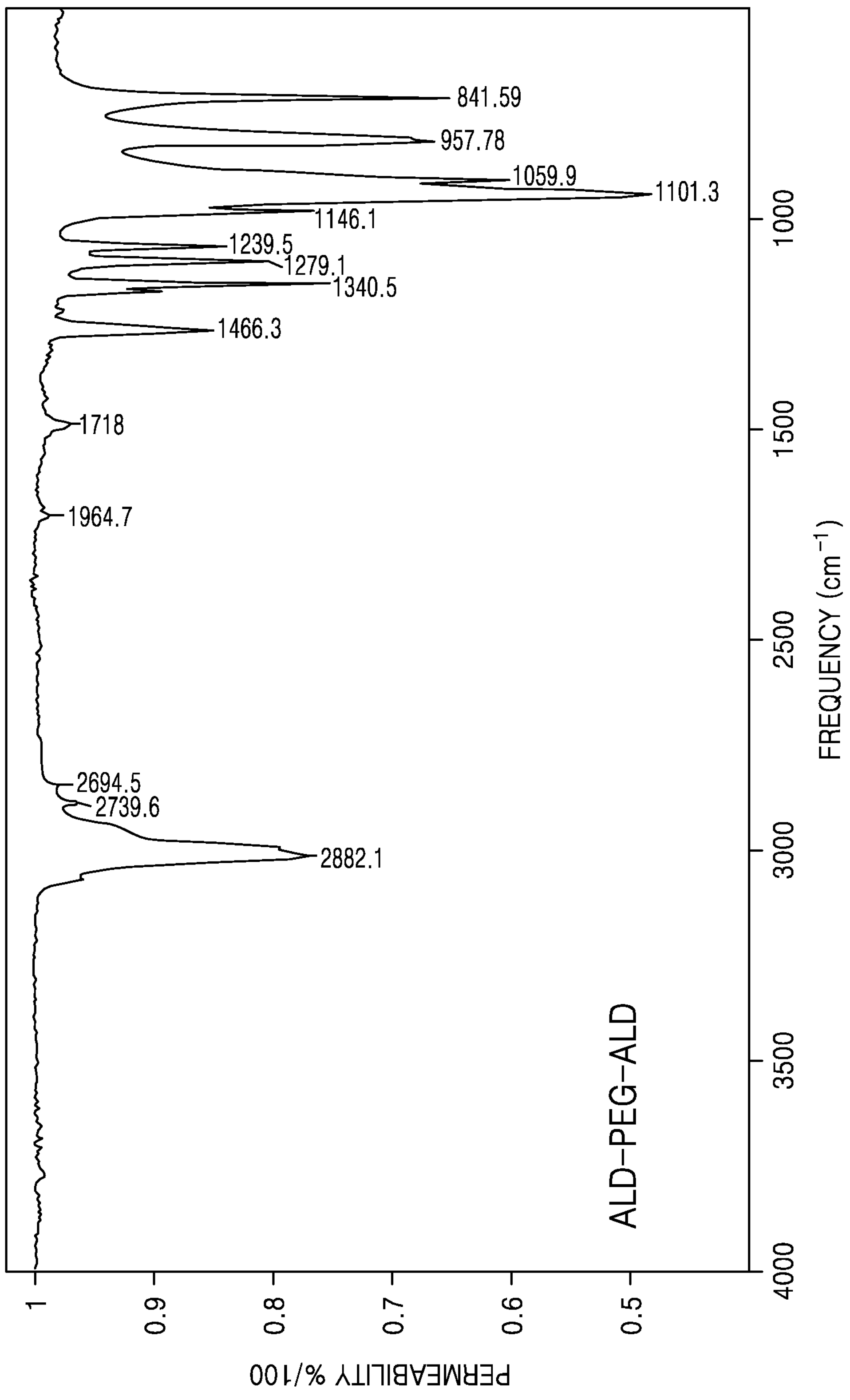

FIGS. 4A and 4B show FT-IR spectra of ALD-PEG-DEP of Experimental Example 2 and commercially available ALD-PEG-ALD, respectively. From the fact that the FT-IR spectra of FIGS. 4A and 4B have similar peak patterns, it can be seen that ALD-PEG-DEP of Experimental Example 2 and commercially available ALD-PEG-ALD have a similar polymer backbone.

The purity of this polyethylene glycol derivative composition including ALD-PEG-DEP was analyzed by high performance liquid chromatography (HPLC). A column filled with octylsilylated silica gel (inner diameter 4.6 mm×length 250 mm, 5.0 μm) was used as the column, and purified water and acetonitrile were used as mobile phases for analysis by reverse-phase chromatography. The content ratio of the polyethylene glycol derivative was calculated as the area ratio of the corresponding peak measured by high performance liquid chromatography.

Example 1: Preparation of CA GLP-2(RK)-PEG-Immunoglobulin Fc Conjugate Using ALD-PEG-DEP

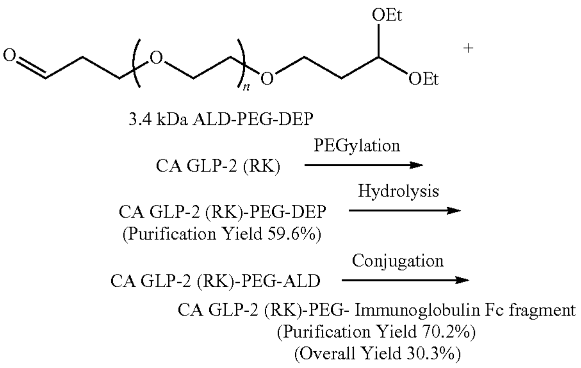

A physiologically active polypeptide conjugate was prepared using the polypeptide CA GLP-2 (RK) of SEQ ID NO: 1, which is a derivative of human glucagon-like peptide-2 (GLP-2) as a physiologically active polypeptide.

The amino acid sequence of the polypeptide CA GLP-2 (RK) of SEQ ID NO: 1 is as follows:

```
(4-imidazoacetyl-Gly-Asp-Gly-Ser-Phe-Ser-Asp-Glu-
Met-Asn-Thr-Ile-Leu-Asp-Asn-Leu-Ala-Ala-Arg-Asp-
Phe-Ile-Asn-Trp-Leu-Ile-Gln-Thr-Arg-Ile-Thr-Asp-
Lys)
```

(1) Preparation of CA GLP-2(RK)-PEG-DEP Conjugate

CA GLP-2(RK)-PEG-DEP was prepared by conjugating the aldehyde terminus of 3.4 kDa ALD-PEG-DEP with lysine residue 34 of CA GLP-2(RK). At this time, the molar ratio of CA GLP-2(RK) and ALD-PEG-ALD was 1:8, and the concentration of CA GLP-2(RK) peptide was 10 mg/mL, and the reaction was carried out at room temperature for about 25 hours. At this time, as the reaction solution, a solution containing 50 mM triethanolamine (pH 8.0) and 100 mM sodium borohydride cyanide ($NaBH_3CN$) as a reducing agent, was used. After completion of the reaction, the reaction mixture was purified by anion exchange chromatography using 20 mM Bis-Tris buffer (pH 6.2) and NaCl concentration gradient. The purification yield was 59.6%, and results of SE-HPLC and RP-HPLC analysis show the purities of 99% and 99%, respectively.

(2) Preparation of CA GLP-2(RK)-PEG-ALD Conjugate

In order to convert the diethoxy functional group (DEP) of purified CA GLP-2(RK)-PEG-DEP into an ALD group by hydrolysis, the pH was lowered using 20 mM sodium citrate (pH 2.0) buffer, followed exchanging the buffer by using the 20 mM bistris (pH 6.5) to obtain CA GLP-2(RK)-PEG-ALD.

(3) Preparation of CA GLP-2(RK)-PEG-Immunoglobulin Fc Conjugate

Next, a conjugation reaction was performed with the molar ratio of CA GLP-2(RK)-PEG-ALD to immunoglobulin Fc fragment (SEQ ID NO: 2) of 1:2, and the total protein (CA GLP-2(RK) and the immunoglobulin Fc fragment) of 30 mg/mL at room temperature for 14 hours to 16 hours. At this time, 20 mM bistris (pH 6.2) and ethanol and 30 mM $NaBH_3CN$ as a reducing agent were added to the reaction solution. After completion of the reaction, CA GLP-2(RK)-PEG-immunoglobulin Fc was purified from the reaction mixture by hydrophobic interaction chromatography (HIC) and anion exchange chromatography. The purification yield was 70.2%, and the analysis results of SE-HPLC and RP-HPLC show the purities of 98.1% and 97%, respectively.

The amino acid sequence of the immunoglobulin Fc of SEQ ID NO: 2 is as follows:

```
(Pro-Ser-Cys-Pro-Ala-Pro-Glu-Phe-Leu-Gly-Gly-Pro-
Ser-Val-Phe-Leu-Phe-Pro-Pro-Lys-Pro-Lys-Asp-Thr-
Leu-Met-Ile-Ser-Arg-Thr-Pro-Glu-Val-Thr-Cys-Val-
Val-Val-Asp-Val-Ser-Gln-Glu-Asp-Pro-Glu-Val-Gln-
Phe-Asn-Trp-Tyr-Val-Asp-Gly-Val-Glu-Val-His-Asn-
Ala-Lys-Thr-Lys-Pro-Arg-Glu-Glu-Gln-Phe-Asn-Ser-
Thr-Tyr-Arg-Val-Val-Ser-Val-Leu-Thr-Val-Leu-His-
Gln-Asp-Trp-Leu-Asn-Gly-Lys-Glu-Tyr-Lys-Cys-Lys-
Val-Ser-Asn-Lys-Gly-Leu-Pro-Ser-Ser-Ile-Glu-Lys-
Thr-Ile-Ser-Lys-Ala-Lys-Gly-Gln-Pro-Arg-Glu-Pro-
Gln-Val-Tyr-Thr-Leu-Pro-Pro-Ser-Gln-Glu-Glu-Met-
Thr-Lys-Asn-Gln-Val-Ser-Leu-Thr-Cys-Leu-Val-Lys-
Gly-Phe-Tyr-Pro-Ser-Asp-Ile-Ala-Val-Glu-Trp-Glu-
Ser-Asn-Gly-Gln-Pro-Glu-Asn-Asn-Tyr-Lys-Thr-Thr-
Pro-Pro-Val-Leu-Asp-Ser-Asp-Gly-Ser-Phe-Phe-Leu-
Tyr-Ser-Arg-Leu-Thr-Val-Asp-Lys-Ser-Arg-Trp-Gln-
Glu-Gly-Asn-Val-Phe-Ser-Cys-Ser-Val-Met-His-Glu-
Ala-Leu-His-Asn-His-Tyr-Thr-Gln-Lys-Ser-Leu-Ser-
Leu-Ser-Leu-Gly-Lys)
```

Comparative Example 1: Preparation of CA GLP-2(RK)-PEG-Immunoglobulin Fc Conjugate Using ALD-PEG-ALD

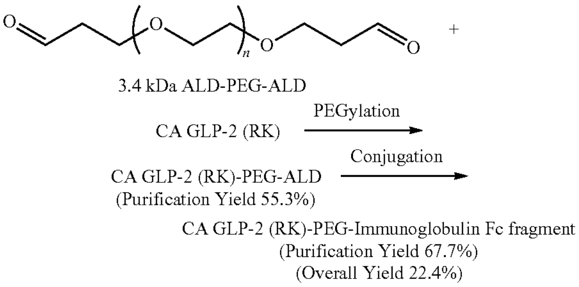

(1) Preparation of CA GLP-2(RK)-PEG-ALD Conjugate

To pegylate 3.4 kDa ALD-PEG-ALD (Hanmi Fine Chemical Corporation, Korea, product name: PGA) to 34th lysine residue of CA GLP-2(RK), the reaction was carried out at room temperature for about 2 hours to about 4 hours with a molar ratio of CA GLP-2(RK) to 3.4 kDa ALD-PEG-ALD of 1:8, and a concentration of CA GLP-2 (RK) of 12 mg/mL. At this time, 50 mM triethanolamine (pH 8.0) and isopropanol and 200 mM 2-picoline borane complex, which was a reducing agent, were added to the reaction solution. After completion of the reaction, the reaction solution was applied to an anion exchange column using a 20 mM bistris (pH 6.2) buffer solution and a sodium chloride concentration gradient to purify CA GLP-2(RK)-PEG-ALD. The purification yield was 55.3%, and results of SE-HPLC and RP-HPLC analysis show the purities of 90% and 87%, respectively.

(2) Preparation of CA GLP-2(RK)-PEG-Immunoglobulin Fc Conjugate

Next, the reaction was carried out with the molar ratio of CA GLP-2(RK)-PEG-ALD to the immunoglobulin Fc fragment (SEQ ID NO: 2) of 1:2, and the concentration of the immunoglobulin Fc fragment of 30 mg/mL at room temperature for 14-16 hours. At this time, a solution containing 20 mM bistris (pH 6.2) and isopropanol and 20 mM 2-picoline borane complex, which was a reducing agent, was used as a reaction solution. After completion of the reaction, CA GLP-2(RK)-PEG-immunoglobulin Fc was purified from the reaction mixture by hydrophobic interaction chromatography (HIC) and anion exchange chromatography. The purification yield was 67.7%, and the analysis results of SE-HPLC and RP-HPLC show the purities of 98.6% and 96.1%, respectively.

Analysis Example: Maintaining the Activity of the Aldehyde Group of Polyethylene Glycol Derivative With respect to the extent (activity) of the aldehyde group remaining until immediately before the conjugation reaction step with the Fc fragment in the method of preparing a physiologically active polypeptide conjugate, Example using the polyethylene glycol derivative of the present disclosure and Comparative Example using a PEG derivative having both ends with an aldehyde group were compared.

With respect to the GLP-2 derivative, which is a physiologically active polypeptide used in the conjugate preparation process of Example 1, pegylation, chromatographic purification, and hydrolysis described in Example 1 were performed to obtain linkage hydrolyzate. With respect to the same physiologically active polypeptide, pegylation and chromatographic purification described in Comparative Example 1 were performed to obtain a corresponding linkage.

Subsequently, the linkage hydrolyzate and the linkage were reacted with a reagent to form a derivative, and the degree of derivative formation was quantified by UV-visible spectrophotometry to measure the activity of the aldehyde group. Results thereof are shown in FIG. 5.

Figure 5:
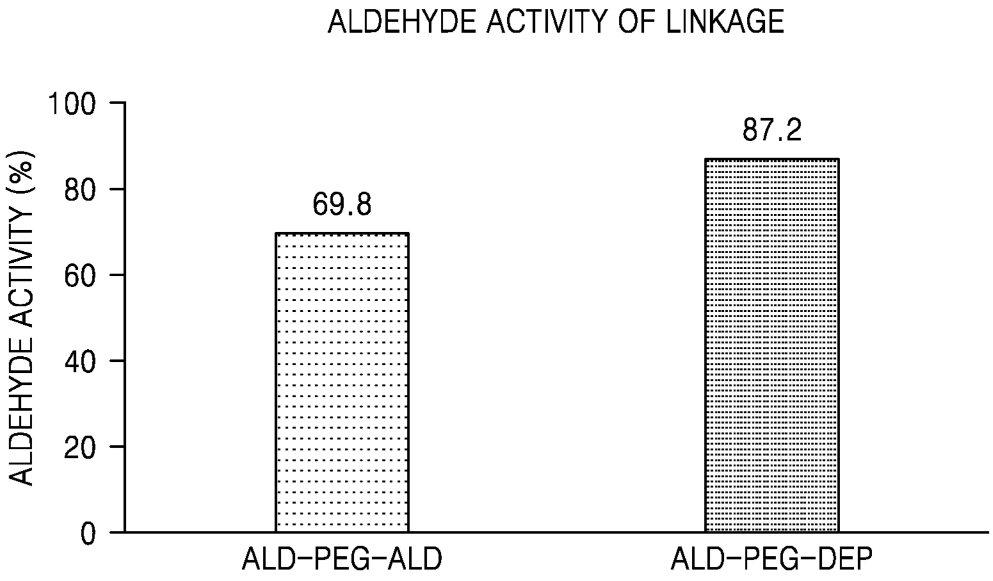
FIG. 5 shows a graph showing the activity of the aldehyde group of the linkage hydrolyzate of Example 1 and the linkage of Comparative Example 1.

Referring to FIG. 5, the aldehyde group activity of the linkage hydrolyzate obtained using ALD-PEG-DEP according to the present disclosure was 87.2%, significantly higher than 69.8%, which was the aldehyde group activity of the linkage obtained using ALD-PEG-ALD of the related art. This results show that the aldehyde group was maintained at a relatively high ratio.

As described above, in the method for preparing a physiologically active polypeptide conjugate using a polyethylene glycol derivative compound according to an embodiment of the present disclosure, the activity of the aldehyde terminus can be maintained higher. Furthermore, even when the same purification process as that of the prior art is used in the subsequent process, the production yield of the conjugation reaction process of the manufacturing method of the present disclosure is improved compared to that of the prior art. In the case of Examples of the present disclosure, the production yield of the conjugation reaction was 50.8%, which is greater than 40.5%, which is the production yield obtained using ALD-PEG-ALD of the prior art, by more than 25%.

In the preparation of the CA GLP-2(RK)-PEG-immunoglobulin Fc conjugate, the total yield in Example 1 of the present disclosure was 30.3%, which is greater than 22.4% of Comparative Example 1 of the prior art by about 35%.

Example 2: Preparation of CA EXD4(Lys27)-PEG-Immunoglobulin Fc Conjugate Using ALD-PEG-DEP

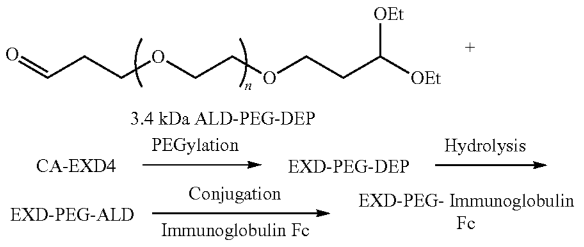

(1) Preparation of CA EXD4-PEG-DEP Conjugate

As a physiologically active polypeptide, imidazoacetyl-exendin-4, a derivative of exendin-4 (Hanmi Fine Chemical Corporation, Korea) (hereinafter referred to as CA EXD4, SEQ ID NO: 3) was used to prepare a physiologically active polypeptide conjugate.

The amino acid sequence of CA EXD4 of SEQ ID NO: 3 is as follows:

(4-imidazoacetyl-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$)

In order to pegylate the 3.4 kDa ALD-PEG-DEP prepared in Experimental Example 1 to the lysine 27 (Lys27) position of CA EXD4, the reaction was carried out with the molar ratio of CA EXD4: ALD-PEG-DEP of 1:3 and the concentration of CA EXD4 of 12 g/L at a temperature of 8±2° C. for about 16 hours. Specifically, the reaction was carried out in 0.1 M bis-tris (pH 7.9), and 45% (v/v) isopropanol, and 50 mM SCB ($NaCNBH_3$, sodium cyanoborohydride) was added thereto as a reducing agent.

After completion of the reaction, CA EXD4(Lys27)-PEG-DEP conjugate was isolated and purified from the reaction solution using a SOURCE 15S column (Cytiva) by applying a buffer solution containing sodium citrate and ethanol and a linear concentration gradient of KCl.

The yield of CA EXD4(Lys27)-PEG-DEP compared to the used CA EXD4 was confirmed to be about 50%.

(2) Preparation of CA EXD4-PEG-ALD Conjugate

In order to hydrolyze the diethoxypropyl (DEP) functional group of the CA EXD4(Lys27)-PEG-DEP conjugate into a propylaldehyde group (ALD), the buffer was exchanged with an acidic solution. Specifically, after diluting CA EXD4(Lys27)-PEG-DEP with water, the buffer solution exchange and concentration were performed using 25 mM hydrochloric acid through the separation membrane ultra/diafiltration (UF/DF) method to isolate the CA EXD4 (Lys27)-PEG-ALD conjugate in such a way that a final recovery concentration was about 0.8 g/L or more. As a result of analyzing the degree of conversion of the terminal functional group using RP-HPLC analysis, it was confirmed that at least 95% of the diethoxypropyl group was converted to the propylaldehyde group.

(3) Preparation of CA EXD4(Lys27)-PEG-Immunoglobulin Fc Conjugate

To prepare a CA EXD4(Lys27)-PEG-immunoglobulin Fc conjugate, the CA EXD4(Lys27)-PEG-ALD conjugate obtained in (2) was conjugated with an immunoglobulin Fc (SEQ ID NO: 2). At this time, the molar ratio of CA EXD4(Lys27)-PEG-ALD conjugate to immunoglobulin Fc was 1:2, and the concentration of total protein (CA EXD4 and immunoglobulin Fc) was 10 g/L, followed by a reaction at room temperature for 2 hours. In this case, a solution containing Bis-Tris and SCB as a reducing agent was used as the reaction solution.

After completion of the reaction, a CA EXD4(Lys27)-PEG-immunoglobulin Fc conjugate was obtained from the reaction mixture by hydrophobic interaction chromatography and anion exchange chromatography.

The yield of the CA EXD4(Lys27)-PEG-immunoglobulin Fc conjugate compared to the injected CA EXD4 physiologically active polypeptide was confirmed to be about 50% to about 60%.

Comparative Example 2: Preparation of CA EXD4(Lys27)-PEG-Immunoglobulin Fc Conjugate Using ALD-PEG-ALD

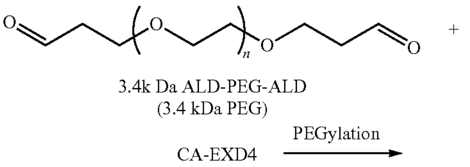

-continued

EXD-PEG-ALD
Conjugation
Immunoglobulin Fc fragment
EXD-PEG- Immunoglobulin Fc fragment (1) Preparation of CA EXD4-PEG-ALD Conjugate To pegylate 3.4 kDa ALD-PEG-ALD (Hanmi Fine Chemical Corporation, Korea) to the Lys27 position of CA EXD4, a derivative of exendin-4, the reaction was carried out with the molar ratio of CA EXD4:PEG of 1:5, and the concentration of CA EXD4 of 18 g/L at a temperature of 8±2° C. for about 4 hours. At this time, the reaction was carried out in 0.1 M HEPES buffer solution (pH 7.5) and 45% isopropanol, and 50 mM SCB ($NaCNBH_3$, sodium cyanoborohydride) was added thereto as a reducing agent.

After completion of the reaction, CA EXD4(Lys27)-PEG-ALD conjugate was isolated and purified from the reaction solution using a SOURCE 15S column (Cytiva) by applying a buffer solution containing sodium citrate and ethanol and a linear concentration gradient of KCl.

Thereafter, after the purified solution of the CA EXD4 (Lys27)-PEG-ALD conjugate was diluted with water, the buffer solution exchange and concentration were performed using a 10 mM potassium phosphate solution through a separation membrane ultra/diafiltration (UF/DF) method to obtain a final recovery concentration of about 0.6 g/L or more.

The yield of CA EXD4(Lys27)-PEG-ALD conjugate compared to the used CA EXD4 physiologically active polypeptide was confirmed to be 35% to 43%.

(2) Preparation of CA EXD4(Lys27)-PEG-Immunoglobulin Fc Conjugate

To prepare a CA EXD4(Lys27)-PEG-immunoglobulin Fc conjugate, the CA EXD4(Lys27)-PEG-ALD conjugate obtained in (1) was conjugated with an immunoglobulin Fc (SEQ ID NO: 2). At this time, the molar ratio of CA EXD4(Lys27)-PEG-ALD conjugate to immunoglobulin Fc was 1:2, and the concentration of total protein (CA EXD4 and immunoglobulin Fc) was 10 g/L, followed by a reaction at room temperature for 16 hours. In this case, a solution containing HEPES and SCB as an ethanol reducing agent was used as the reaction solution.

After completion of the reaction, a CA EXD4(Lys27)-PEG-immunoglobulin Fc conjugate was obtained from the reaction mixture by hydrophobic interaction chromatography and anion exchange chromatography. The yield with respect to the input physiologically active polypeptide was confirmed to be 35% to 40%.

With respect to the total yield of CA-EXD4-PEG-immunoglobulin Fc production, the yield of Example 2 was greater than the yield of Comparative Example 2.

Example 3: Preparation of GCSF Derivative-PEG-Immunoglobulin Fc Conjugate Using ALD-PEG-DEP

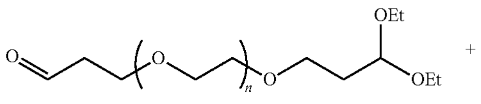

3.4 kDa ALD-PEG-DEP

-continued

GCSF
PEGylation
GCSF-PEG-DEP
Hydrolysis
GCSF-PEG-ALD
Conjugation
Immunoglobulin Fc fragment
GCSF-PEG-Immunoglobulin Fc fragment (1) Preparation of GCSF-PEG-DEP A physiologically active polypeptide conjugate was prepared using a derivative (SEQ ID NO: 4) of human granulocyte colony stimulating factor (GCSF) as a physiologically active polypeptide.

The amino acid sequence of the GCSF derivative of SEQ ID NO: 4 is as follows:

```
(TPLGPASSLP QSFLLKSLEQ VRKIQGDGAA LQEKLCATYK
LCHPEELVLL GHSLGIPWAP LSSCSSQALQ LAGCLSQLHS
GLFLYQGLLQ ALEGISPELG PTLDTLQLDV ADFATTIWQQ
MEELGMAPAL QPTQGAMPAF ASAFQRRAGG VLVASHLQSF
LEVSYRVLRH LAQP)
```

In order to pegylate the 3.4 kDa ALD-PEG-DEP prepared in Experimental Example 1 to the N-terminal threonine position of the GCSF derivative, the reaction was carried out with the molar ratio of the GCSF derivative: ALD-PEG-DEP of 1:4 and the concentration of the GCSF derivative of 8 g/L at a temperature of 6±4° C. for 8 hours. Specifically, the reaction was carried out in 0.1 M potassium phosphate (pH 6.0), and 50 mM SCB was added as a reducing agent.

After the binding reaction, the GCSF derivative-PEG-DEP was purified using an SP-HP column (Cytiva, cation exchange chromatography). At this time, sodium acetate buffer solution was used, and purification was performed using a sodium chloride concentration gradient.

The yield of GCSF-PEG-DEP compared to the added GCSF derivative was found to be 61.2%.

(2) Hydrolysis of DEP Functional Groups

Buffer solution exchange was performed with an acidic solution to hydrolyze the DEP functional group of the GCSF derivative-PEG-DEP into a propyl aldehyde group (ALD). Specifically, the purified GCSF-PEG-DEP was stored at room temperature for 16 hours after the pH of the buffer was lowered to 2.0 through the separation membrane ultra/diafiltration (UF/DF) method.

(3) Preparation of GCSF Derivative-PEG-Immunoglobulin Fc Conjugate

To prepare a GCSF-PEG-immunoglobulin Fc conjugate, the GCSF derivative-PEG-ALD obtained in (2) was conjugated with immunoglobulin Fc (SEQ ID NO: 2). At this time, the reaction was carried out with the molar ratio of the GCSF derivative-PEG-ALD linkage and the immunoglobulin Fc of 1:4 and the total protein (GCSF and immunoglobulin Fc) concentration of 50 g/L at a temperature of 6±4° C. for 16 hours. Specifically, the reaction was carried out in 0.1 M potassium phosphate (pH 6.0), and 20 mM SCB was added as a reducing agent.

After completion of the reaction, a GCSF derivative-PEG-immunoglobulin Fc conjugate was obtained from the reaction mixture by hydrophobic interaction chromatography and anion exchange chromatography.

The yield of the GCSF derivative-PEG-immunoglobulin Fc conjugate with respect to the used GCSF derivative-PEG-DEP was confirmed to be 50.2%.

Comparative Example 3: Preparation of GCSF Derivative-PEG-Immunoglobulin Fc Conjugate Using ALD-PEG-ALD

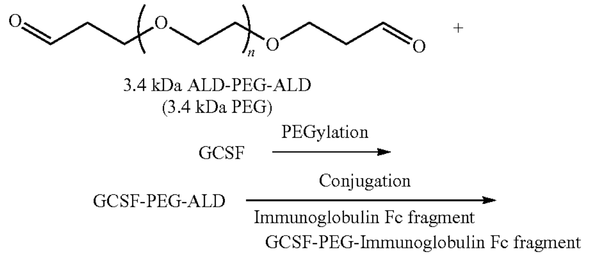

(1) Preparation of GCSF-PEG-ALD

In order to pegylate 3.4 kDa ALD-PEG-ALD (NOF) to the N-terminal threonine position of the GCSF derivative (SEQ ID NO: 4), the reaction was carried out with the molar ratio of the GCSF derivative: ALD-PEG-ALD of 1:10 and the concentration of the GCSF derivative of 5 g/L at a temperature of 6±4° C. for 1.5 hours. Specifically, the reaction was carried out in 0.1 M potassium phosphate (pH 6.0), and 20 mM SCB was added as a reducing agent.

After the binding reaction, the GCSF derivative-PEG-ALD linkage was purified using an SP-HP column (Cytiva, cation exchange chromatography). At this time, sodium acetate buffer solution was used, and purification was performed using a sodium chloride concentration gradient.

The yield of GCSF derivative-PEG-ALD linkage with respect to the added GCSF derivative was found to be 56.5%.

(2) Preparation of GCSF Derivative-PEG-Immunoglobulin Fc Conjugate

To prepare a GCSF derivative-PEG-immunoglobulin Fc conjugate, the GCSF derivative-PEG-ALD was conjugated with immunoglobulin Fc (SEQ ID NO: 2). At this time, the reaction was carried out with the molar ratio of the GCSF-PEG-ALD linkage and the immunoglobulin Fc of 1:4, and the total protein (GCSF derivative and immunoglobulin Fc) concentration of 50 g/L at a temperature of 6±4° C. for 16 hours. Specifically, the reaction was carried out in 0.1 M potassium phosphate (pH 6.0), and 20 mM SCB was added as a reducing agent.

After completion of the reaction, a GCSF derivative-PEG-immunoglobulin Fc conjugate was obtained from the reaction mixture by hydrophobic interaction chromatography and anion exchange chromatography.

The yield of GCSF derivative-PEG-DEP conjugate with respect to the added GCSF derivative was found to be 39.9%.

When comparing the total yield of the preparation of GCSF derivative-PEG-immunoglobulin Fc conjugate, Example 3 according to the present disclosure provided 1.36 times greater yield than Comparative Example 3 of the prior art.

The invention claimed is:

1. A polyethylene glycol derivative compound of Formula 1:

Formula 1

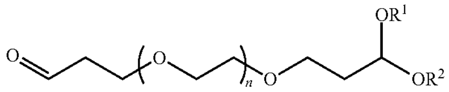

wherein, in Formula 1, n is a natural number of 30 to 115, and $R^1$ and $R^2$ are $C_1$-$C_5$ alkyl that are identical to or different from each other.

2. The polyethylene glycol derivative compound of claim 1, wherein the $C_1$ to Cs alkyl are methyl, ethyl, propyl, or butyl.

3. The polyethylene glycol derivative compound of claim 1, wherein $R^1$ and $R^2$ are each ethyl.

4. The polyethylene glycol derivative compound of according to claim 1, wherein n is a natural number from 50 to 100.

5. The compound of claim 4, wherein n is a natural number from 67 to 83.

6. A polyethylene glycol derivative composition comprising:

a polyethylene glycol derivative represented by Formula 1A;

a polyethylene glycol derivative represented by Formula 2; and a polyethylene glycol derivative represented by Formula 3:

Formula 1A

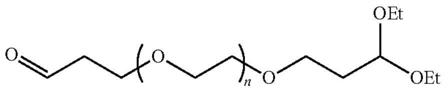

-continued

Formula 2

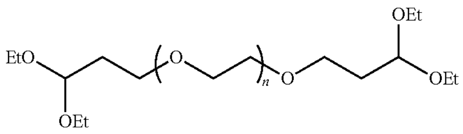

Formula 3

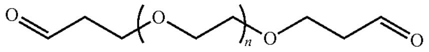

wherein, in the composition, a content ratio of the polyethylene glycol derivative represented by Formula 1A within a range of number average molecular weight of 2950 to 3650 is at least 70 area % based on high performance liquid chromatography (HPLC), a content ratio of the polyethylene glycol derivative represented by Formula 2 within a range of number average molecular weight of 2950 to 3650 is 15 area % or less based on HPLC, and a content ratio of the polyethylene glycol derivative represented by Formula 3 within a range of number average molecular weight of 2950 to 3650 is 10 area % or less based on HPLC.

7. The polyethylene glycol derivative composition of claim 6, wherein the number average molecular weight of each of the polyethylene glycol derivatives is in a range of 2950 to 3650, the measurements obtained by gel permeation chromatography.

8. The polyethylene glycol derivative composition of claim 7, wherein the number average molecular weight of each of the polyethylene glycol derivatives is in a range of 3000 to 3200, the measurements obtained by gel permeation chromatography.

9. A method of preparing a physiologically active polypeptide conjugate, the method comprising:

(a) a pegylation process in which a polyethylene glycol derivative of Formula 1 is reacted with a physiologically active polypeptide to generate a linkage in which the physiologically active polypeptide is covalently conjugated with an aldehyde carbon of the polyethylene glycol derivative of Formula 1;

(b) a hydrolysis process in which the linkage is treated in an acidic aqueous condition to form a linkage hydrolyzate; and (c) a conjugation process in which the linkage hydrolyzate is reacted with an immunoglobulin Fc fragment or a derivative thereof to generate a conjugate, wherein the conjugate has a structure in which the Fc fragment or the derivative thereof is covalently conjugated with a carbon atom derived from an acetal carbon of the polyethylene glycol derivative of Formula 1 in the linkage hydrolyzate:

Formula 1

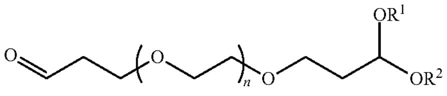

wherein, in Formula 1, n is a natural number of 50 to 100, and $R^1$ and $R^2$ are $C_1$-$C_5$ alkyl that are identical to or different from each other.

10. The method of preparing a physiologically active polypeptide conjugate of claim 9, wherein the physiologically active polypeptide is selected from hormones, cytokines, enzymes, antibodies, growth factors, transcriptional regulators, blood coagulation factors, vaccines, structural proteins, ligand proteins, and receptors.

11. The method of preparing a physiologically active polypeptide conjugate of claim 9, wherein the reaction of process (a) is reductive amination, and the linkage is a material in which an N-terminal nitrogen of the physiologically active polypeptide or a nitrogen atom of an ε-amino group of lysine is covalently conjugated with the aldehyde carbon atom of the compound of Formula 1.

12. The method of preparing a physiologically active polypeptide conjugate of claim 11, wherein the pegylation of process (a) is carried out at a pH of 3.0 to 9.0.

13. The method of preparing a physiologically active polypeptide conjugate of claim 11, wherein the hydrolysis in process (b) is performed at a pH of 1.0 to 5.0.

14. The method of preparing a physiologically active polypeptide conjugate of claim 9, wherein the conjugation reaction in process (c) is reductive amination.

15. The method of preparing a physiologically active polypeptide conjugate of claim 14, wherein the reductive amination is carried out at a pH of 5.0 to 8.5.

16. The method of preparing a physiologically active polypeptide conjugate of claim 9, wherein the sequence of the Fc fragment or the derivative thereof at the N-terminus is proline.

17. The method of preparing a physiologically active polypeptide conjugate of claim 16, wherein in the conjugate, a nitrogen atom of the N-terminal proline of the Fc fragment or the derivative thereof is covalently conjugated with a carbon atom derived from the acetal carbon.

18. The method of preparing a physiologically active polypeptide conjugate of claim 17, wherein the Fc fragment or the derivative thereof has a SEQ ID NO: 2.

19. The method of preparing a physiologically active polypeptide conjugate of claim 9, wherein $R^1$ and $R^2$ are each ethyl.

20. The method of preparing a physiologically active polypeptide conjugate of claim 9, wherein n is a natural number from 67 to 83.

* * * * *

SEQUENCE LISTING

```
<160> NUMBER OF SEQ ID NOS: 4

<210> SEQ ID NO 1
<211> LENGTH: 34
<212> TYPE: PRT
<213> ORGANISM: Artificial Sequence
<220> FEATURE:
<223> OTHER INFORMATION: Human Glucagon-like peptide-2 derivative
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 1

Xaa Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Arg Ile Thr
            20                  25                  30

Asp Lys


<210> SEQ ID NO 2
<211> LENGTH: 221
<212> TYPE: PRT
<213> ORGANISM: Artificial Sequence
<220> FEATURE:
<223> OTHER INFORMATION: Human Immunoglobulin Fc fragment

<400> SEQUENCE: 2

Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
```

-continued

```
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220


<210> SEQ ID NO 3
<211> LENGTH: 39
<212> TYPE: PRT
<213> ORGANISM: Artificial Sequence
<220> FEATURE:
<223> OTHER INFORMATION: imidazoacetyl-Exendin-4
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (39)
<223> OTHER INFORMATION: Ser is modified to have -NH2 group

<400> SEQUENCE: 3

Xaa Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35


<210> SEQ ID NO 4
<211> LENGTH: 174
<212> TYPE: PRT
<213> ORGANISM: Artificial Sequence
<220> FEATURE:
<223> OTHER INFORMATION: granulocyte colony stimulating factor, GCSF

<400> SEQUENCE: 4

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
```

-continued

```
        35                  40                  45

Leu Leu Gly His Ser Leu Gly Ile Pro Trp Ala Pro Leu Ser Ser Cys
    50                  55                  60

Ser Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```